US009808300B2

(12) United States Patent
Hastings et al.

(10) Patent No.: US 9,808,300 B2
(45) Date of Patent: Nov. 7, 2017

(54) CONTROL OF ARTERIAL SMOOTH MUSCLE TONE

(71) Applicant: Boston Scientific Scimed, Inc., Maple Grove, MN (US)

(72) Inventors: Roger Hastings, Maple Grove, MN (US); William J. Drasler, Minnetonka, MN (US); Vitaly N. Shapovalov, New Hope, MN (US); Mark Schroeder, Fargo, ND (US); Anupama Sadasiva, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 53 days.

(21) Appl. No.: 13/770,052

(22) Filed: Feb. 19, 2013

(65) Prior Publication Data

US 2013/0172882 A1 Jul. 4, 2013

Related U.S. Application Data

(63) Continuation of application No. 13/226,732, filed on Sep. 7, 2011, now Pat. No. 8,391,971, which is a continuation of application No. 11/381,238, filed on May 2, 2006, now Pat. No. 8,019,435.

(51) Int. Cl.
*A61N 1/36* (2006.01)
*A61B 18/00* (2006.01)
*A61N 1/05* (2006.01)

(52) U.S. Cl.
CPC ................ *A61B 18/00* (2013.01); *A61N 1/05* (2013.01); *A61N 1/36017* (2013.01); *A61N 1/36007* (2013.01); *A61N 1/36117* (2013.01)

(58) Field of Classification Search
CPC . A61N 1/36117; A61N 1/0551; A61N 1/3605
USPC ........................................................... 607/44
See application file for complete search history.

(56) References Cited

U.S. PATENT DOCUMENTS

| | | | |
|---|---|---|---|
| 164,184 | A | 6/1875 | Kiddee |
| 852,787 | A | 5/1907 | Hoerner |
| 921,973 | A | 5/1909 | Gillett et al. |
| 976,733 | A | 11/1910 | Gilliland |
| 1,167,014 | A | 1/1916 | O'Brien |
| 2,505,358 | A | 4/1950 | Gusberg et al. |
| 2,701,559 | A | 2/1955 | Cooper |

(Continued)

FOREIGN PATENT DOCUMENTS

| | | | |
|---|---|---|---|
| DE | 10038737 | A1 | 2/2002 |
| EP | 1053720 | A1 | 11/2000 |

(Continued)

OTHER PUBLICATIONS

US 8,398,630, 03/2013, Demarais et al. (withdrawn)

(Continued)

*Primary Examiner* — Eric D. Bertram

(57) ABSTRACT

An apparatus for locally controlling smooth muscle tone includes a first electrode for insertion into an artery; a barrier for preventing the first electrode from contacting an arterial wall; a second electrode; a power supply; and a controller for coupling the power supply to the electrodes. The controller is configured to cause the electrode to maintain a waveform for controlling polarization of smooth muscle tone.

18 Claims, 14 Drawing Sheets

(56) References Cited

U.S. PATENT DOCUMENTS 3,108,593 A 10/1963 Glassman
3,108,594 A 10/1963 Glassman
3,540,431 A 11/1970 Mobin
3,952,747 A 4/1976 Kimmell
3,996,938 A 12/1976 Clark, III
4,046,150 A 9/1977 Schwartz et al.
4,290,427 A 9/1981 Chin
4,402,686 A 9/1983 Medel
4,483,341 A 11/1984 Witteles et al.
4,531,943 A 7/1985 Van Tassel et al.
4,574,804 A 3/1986 Kurwa
4,587,975 A 5/1986 Salo et al.
4,649,936 A 3/1987 Ungar et al.
4,682,596 A 7/1987 Bales et al.
4,709,698 A 12/1987 Johnston et al.
4,765,331 A 8/1988 Petruzzi et al.
4,770,653 A 9/1988 Shturman
4,784,132 B1 11/1988 Fox et al.
4,784,162 A 11/1988 Ricks et al.
4,785,806 A 11/1988 Deckelbaum et al.
4,788,975 B1 12/1988 Shturman et al.
4,790,310 A 12/1988 Ginsburg et al.
4,799,479 A 1/1989 Spears
4,823,791 A 4/1989 D'Amelio et al.
4,830,003 A 5/1989 Wolff et al.
4,849,484 A 7/1989 Heard
4,862,886 A 9/1989 Clarke et al.
4,887,605 A 12/1989 Angelsen et al.
4,890,623 A 1/1990 Cook et al.
4,920,979 A 5/1990 Bullara et al.
4,938,766 A 7/1990 Jarvik
4,955,377 A 9/1990 Lennox et al.
4,976,711 A 12/1990 Parins et al.
5,034,010 A 7/1991 Kittrell et al.
5,052,402 A 10/1991 Bencini et al.
5,053,033 A 10/1991 Clarke et al.
5,071,424 A 12/1991 Reger et al.
5,074,871 A 12/1991 Groshong et al.
5,098,429 A 3/1992 Sterzer et al.
5,098,431 A 3/1992 Rydell
5,109,859 A 5/1992 Jenkins
5,125,928 A 6/1992 Parins et al.
5,129,396 A 7/1992 Rosen et al.
5,139,496 A 8/1992 Hed
5,143,836 A 9/1992 Hartman et al.
5,156,610 A 10/1992 Reger et al.
5,158,564 A 10/1992 Schnepp-Pesch
5,170,802 A 12/1992 Mehra
5,178,620 A 1/1993 Eggers et al.
5,178,625 A 1/1993 Groshong et al.
5,190,540 A 3/1993 Lee
5,211,651 A 5/1993 Reger et al.
5,234,407 A 8/1993 Teirstein et al.
5,242,441 A 9/1993 Avitall
5,251,634 A 10/1993 Weinberg et al.
5,255,679 A 10/1993 Imran
5,263,493 A 11/1993 Avitall
5,267,954 A 12/1993 Nita et al.
5,277,201 A 1/1994 Stern et al.
5,282,484 A 2/1994 Reger et al.
5,286,254 A 2/1994 Shapland et al.
5,290,306 A 3/1994 Trotta et al.
5,295,484 A 3/1994 Marcus
5,297,564 A 3/1994 Love et al.
5,300,068 A 4/1994 Rosar et al.
5,301,683 A 4/1994 Durkan
5,304,115 A 4/1994 Pflueger et al.
5,304,121 A 4/1994 Sahatjian
5,304,171 A 4/1994 Gregory et al.
5,304,173 A 4/1994 Kittrell et al.
5,306,250 A 4/1994 March et al.
5,312,328 A 5/1994 Nita et al.
5,314,466 A 5/1994 Stern et al.
5,322,064 A 6/1994 Lundquist
5,324,255 A 6/1994 Passafaro et al.
5,326,341 A 7/1994 Lew et al.
5,326,342 A 7/1994 Plueger et al.
5,330,518 A 7/1994 Neilson et al.
5,333,614 A 8/1994 Feiring
5,342,292 A 8/1994 Nita et al.
5,344,395 A 9/1994 Whalen et al.
5,364,392 A 11/1994 Warner et al.
5,365,172 A 11/1994 Hrovat et al.
5,368,557 A 11/1994 Nita et al.
5,368,558 A 11/1994 Nita et al.
5,380,274 A 1/1995 Nita et al.
5,380,319 A 1/1995 Saito et al.
5,382,228 A 1/1995 Nita et al.
5,383,874 A 1/1995 Jackson et al.
5,383,917 A 1/1995 Desai et al.
5,397,301 A 3/1995 Pflueger et al.
5,397,339 A 3/1995 Desai
5,401,272 A 3/1995 Perkins et al.
5,403,311 A 4/1995 Abele et al.
5,405,318 A 4/1995 Nita et al.
5,405,346 A 4/1995 Grundy et al.
5,409,000 A 4/1995 Imran
5,411,540 A 5/1995 Edell et al.
5,417,672 A 5/1995 Nita et al.
5,419,767 A 5/1995 Eggers et al.
5,427,118 A 6/1995 Nita et al.
5,432,876 A 7/1995 Appeldorn et al.
5,441,498 A 8/1995 Perkins et al.
5,447,509 A 9/1995 Mills et al.
5,451,207 A 9/1995 Yock et al.
5,453,091 A 9/1995 Taylor et al.
5,454,788 A 10/1995 Walker et al.
5,454,809 A 10/1995 Janssen
5,455,029 A 10/1995 Hartman et al.
5,456,682 A 10/1995 Edwards et al.
5,457,042 A 10/1995 Hartman et al.
5,471,982 A 12/1995 Edwards et al.
5,474,530 A 12/1995 Passafaro et al.
5,478,351 A 12/1995 Meade et al.
5,496,311 A 3/1996 Abele et al.
5,496,312 A 3/1996 Klicek et al.
5,498,261 A 3/1996 Strul
5,505,201 A * 4/1996 Grill, Jr. .................. A61N 1/04
600/371
5,505,730 A 4/1996 Edwards
5,507,744 A 4/1996 Tay et al.
5,512,051 A 4/1996 Wang et al.
5,522,873 A 6/1996 Jackman et al.
5,531,520 A 7/1996 Grimson et al.
5,540,656 A 7/1996 Pflueger et al.
5,540,679 A 7/1996 Fram et al.
5,540,681 A 7/1996 Strul et al.
5,542,917 A 8/1996 Nita et al.
5,545,161 A 8/1996 Imran
5,562,100 A 10/1996 Kittrell et al.
5,571,122 A 11/1996 Kelly et al.
5,571,151 A 11/1996 Gregory
5,573,531 A 11/1996 Gregory et al.
5,573,533 A 11/1996 Strul
5,584,831 A 12/1996 McKay
5,584,872 A 12/1996 Lafontaine et al.
5,588,962 A 12/1996 Nicholas et al.
5,599,346 A 2/1997 Edwards et al.
5,601,526 A 2/1997 Chapelon et al.
5,609,606 A 3/1997 O'Boyle et al.
5,613,979 A 3/1997 Trotta et al.
5,626,576 A 5/1997 Janssen
5,630,837 A 5/1997 Crowley
5,637,090 A 6/1997 McGee et al.
5,643,255 A 7/1997 Organ
5,643,297 A 7/1997 Nordgren et al.
5,647,847 A 7/1997 Lafontaine et al.
5,649,923 A 7/1997 Gregory et al.
5,651,780 A 7/1997 Jackson et al.
5,653,684 A 8/1997 Laptewicz et al.
5,662,671 A 9/1997 Barbut et al.
5,665,062 A 9/1997 Houser
5,665,098 A 9/1997 Kelly et al.
5,666,964 A 9/1997 Meilus

(56) References Cited

U.S. PATENT DOCUMENTS 5,667,490 A 9/1997 Keith et al.
5,672,174 A 9/1997 Gough et al.
5,676,693 A 10/1997 Lafontaine
5,678,296 A 10/1997 Fleischhacker et al.
5,681,282 A 10/1997 Eggers et al.
RE35,656 E 11/1997 Feinberg
5,687,737 A 11/1997 Branham et al.
5,688,266 A 11/1997 Edwards et al.
5,693,015 A 12/1997 Walker et al.
5,693,029 A 12/1997 Leonhardt et al.
5,693,043 A 12/1997 Kittrell et al.
5,693,082 A 12/1997 Warner et al.
5,695,504 A 12/1997 Gifford et al.
5,697,369 A 12/1997 Long, Jr. et al.
5,697,909 A 12/1997 Eggers et al.
5,702,386 A 12/1997 Stern et al.
5,702,433 A 12/1997 Taylor et al.
5,706,809 A 1/1998 Littmann et al.
5,713,942 A 2/1998 Stern et al.
5,715,819 A 2/1998 Svenson et al.
5,735,846 A 4/1998 Panescu et al.
5,741,214 A 4/1998 Ouchi et al.
5,741,248 A 4/1998 Stern et al.
5,741,249 A 4/1998 Moss et al.
5,743,903 A 4/1998 Stern et al.
5,748,347 A 5/1998 Erickson
5,749,914 A 5/1998 Janssen
5,755,682 A 5/1998 Knudson et al.
5,755,715 A 5/1998 Stern et al.
5,755,753 A 5/1998 Knowlton et al.
5,769,847 A 6/1998 Panescu et al.
5,769,880 A 6/1998 Truckai et al.
5,775,338 A 7/1998 Hastings
5,776,174 A 7/1998 Van Tassel
5,779,698 A 7/1998 Clayman et al.
5,782,760 A 7/1998 Schaer
5,785,702 A 7/1998 Murphy et al.
5,797,849 A 8/1998 Vesely et al.
5,797,903 A 8/1998 Swanson et al.
5,800,464 A 9/1998 Kieval
5,800,484 A 9/1998 Gough et al.
5,800,494 A 9/1998 Campbell et al.
5,807,306 A 9/1998 Shapland et al.
5,810,802 A 9/1998 Panescu et al.
5,810,803 A 9/1998 Moss et al.
5,810,810 A 9/1998 Tay et al.
5,814,079 A 9/1998 Kieval
5,817,092 A 10/1998 Behl
5,817,113 A 10/1998 Gifford et al.
5,817,144 A 10/1998 Gregory et al.
5,823,956 A 10/1998 Roth et al.
5,827,203 A 10/1998 Nita et al.
5,827,268 A 10/1998 Laufer
5,829,447 A 11/1998 Stevens et al.
5,830,213 A 11/1998 Panescu et al.
5,830,222 A 11/1998 Makower
5,832,228 A 11/1998 Holden et al.
5,833,593 A 11/1998 Liprie
5,836,874 A 11/1998 Swanson et al.
5,840,076 A 11/1998 Swanson et al.
5,843,016 A 12/1998 Lugnani et al.
5,846,238 A 12/1998 Jackson et al.
5,846,239 A 12/1998 Swanson et al.
5,846,245 A 12/1998 McCarthy et al.
5,848,969 A 12/1998 Panescu et al.
5,853,411 A 12/1998 Whayne et al.
5,855,614 A 1/1999 Stevens et al.
5,860,974 A 1/1999 Abele
5,865,801 A 2/1999 Houser
5,868,735 A 2/1999 Lafontaine et al.
5,868,736 A 2/1999 Swanson et al.
5,871,483 A 2/1999 Jackson et al.
5,871,524 A 2/1999 Knowlton et al.
5,875,782 A 3/1999 Ferrari et al.
5,876,369 A 3/1999 Houser
5,876,374 A 3/1999 Alba et al.
5,876,397 A 3/1999 Edelman et al.
5,879,348 A 3/1999 Owens et al.
5,891,114 A 4/1999 Chien et al.
5,891,135 A 4/1999 Jackson et al.
5,891,136 A 4/1999 McGee et al.
5,891,138 A 4/1999 Tu et al.
5,895,378 A 4/1999 Nita
5,897,552 A 4/1999 Edwards et al.
5,902,328 A 5/1999 Lafontaine et al.
5,904,651 A 5/1999 Swanson et al.
5,904,667 A 5/1999 Falwell et al.
5,904,697 A 5/1999 Gifford et al.
5,904,709 A 5/1999 Arndt et al.
5,906,614 A 5/1999 Stern et al.
5,906,623 A 5/1999 Peterson
5,906,636 A 5/1999 Casscells et al.
5,916,192 A 6/1999 Nita et al.
5,916,227 A 6/1999 Keith et al.
5,916,239 A 6/1999 Geddes et al.
5,919,219 A 7/1999 Knowlton et al.
5,924,424 A 7/1999 Stevens et al.
5,925,038 A 7/1999 Panescu et al.
5,934,284 A 8/1999 Plaia et al.
5,935,063 A 8/1999 Nguyen
5,938,670 A 8/1999 Keith et al.
5,947,977 A 9/1999 Slepian et al.
5,948,011 A 9/1999 Knowlton et al.
5,951,494 A 9/1999 Wang et al.
5,951,539 A 9/1999 Nita et al.
5,954,717 A 9/1999 Behl et al.
5,957,882 A 9/1999 Nita et al.
5,957,941 A 9/1999 Ream et al.
5,957,969 A 9/1999 Warner et al.
5,961,513 A 10/1999 Swanson et al.
5,964,757 A 10/1999 Ponzi et al.
5,967,976 A 10/1999 Larsen et al.
5,967,978 A 10/1999 Littmann et al.
5,967,984 A 10/1999 Chu et al.
5,971,975 A 10/1999 Mills et al.
5,972,026 A 10/1999 Laufer et al.
5,980,563 A 11/1999 Tu et al.
5,989,208 A 11/1999 Nita et al.
5,989,284 A 11/1999 Laufer
5,993,462 A 11/1999 Pomeranz et al.
5,997,497 A 12/1999 Nita et al.
5,999,678 A 12/1999 Murphy et al.
6,004,269 A 12/1999 Crowley et al.
6,004,316 A 12/1999 Laufer et al.
6,007,514 A 12/1999 Nita
6,010,522 A 1/2000 Barbut et al.
6,013,033 A 1/2000 Berger et al.
6,014,590 A 1/2000 Whayne et al.
6,022,309 A 2/2000 Celliers et al.
6,024,740 A 2/2000 Lesh
6,030,611 A 2/2000 Gorecki et al.
6,032,675 A 3/2000 Rubinsky et al.
6,033,397 A 3/2000 Laufer et al.
6,033,398 A 3/2000 Farley et al.
6,036,687 A 3/2000 Laufer et al.
6,036,689 A 3/2000 Tu et al.
6,041,260 A 3/2000 Stern et al.
6,050,994 A 4/2000 Sherman et al.
6,056,744 A 5/2000 Edwards
6,056,746 A 5/2000 Goble et al.
6,063,085 A 5/2000 Tay et al.
6,066,096 A 5/2000 Smith et al.
6,066,139 A 5/2000 Ryan et al.
6,068,638 A 5/2000 Makower
6,068,653 A 5/2000 Lafontaine
6,071,277 A 6/2000 Farley et al.
6,071,278 A 6/2000 Panescu et al.
6,078,839 A 6/2000 Carson
6,079,414 A 6/2000 Roth
6,080,171 A 6/2000 Keith et al.
6,081,749 A 6/2000 Ingle et al.
6,086,581 A 7/2000 Reynolds et al.
6,091,995 A 7/2000 Ingle et al.
6,093,166 A 7/2000 Knudson et al.

(56) References Cited

U.S. PATENT DOCUMENTS 6,096,021 A 8/2000 Helm et al.
6,099,526 A 8/2000 Whayne et al.
6,102,908 A 8/2000 Tu et al.
6,106,477 A 8/2000 Miesel et al.
6,106,546 A 8/2000 Gregory
6,110,187 A 8/2000 Donlon et al.
6,110,192 A 8/2000 Ravenscroft et al.
6,114,311 A 9/2000 Parmacek et al.
6,117,101 A 9/2000 Diederich et al.
6,117,128 A 9/2000 Gregory
6,120,476 A 9/2000 Fung et al.
6,120,516 A 9/2000 Selmon et al.
6,121,775 A 9/2000 Pearlman
6,123,679 A 9/2000 Lafaut et al.
6,123,682 A 9/2000 Knudson et al.
6,123,702 A 9/2000 Swanson et al.
6,123,703 A 9/2000 Tu et al.
6,123,718 A 9/2000 Tu et al.
6,129,725 A 10/2000 Tu et al.
6,135,997 A 10/2000 Laufer et al.
6,142,991 A 11/2000 Schatzberger et al.
6,142,993 A 11/2000 Whayne et al.
6,149,647 A 11/2000 Tu et al.
6,152,899 A 11/2000 Farley et al.
6,152,912 A 11/2000 Jansen et al.
6,156,046 A 12/2000 Passafaro et al.
6,158,250 A 12/2000 Tibbals et al.
6,159,187 A 12/2000 Park et al.
6,159,225 A 12/2000 Makower
6,161,048 A 12/2000 Sluijter et al.
6,162,184 A 12/2000 Swanson et al.
6,165,163 A 12/2000 Chien et al.
6,165,172 A 12/2000 Farley et al.
6,165,187 A 12/2000 Reger et al.
6,168,594 B1 1/2001 Lafontaine et al.
6,171,321 B1 1/2001 Gifford, III et al.
6,179,832 B1 1/2001 Jones et al.
6,179,835 B1 1/2001 Panescu et al.
6,179,859 B1 1/2001 Bates et al.
6,183,468 B1 2/2001 Swanson et al.
6,183,486 B1 2/2001 Snow et al.
6,190,379 B1 2/2001 Heuser et al.
6,191,862 B1 2/2001 Swanson et al.
6,197,021 B1 3/2001 Panescu et al.
6,200,266 B1 3/2001 Shokrollahi et al.
6,203,537 B1 3/2001 Adrian
6,203,561 B1 3/2001 Ramee et al.
6,210,406 B1 4/2001 Webster
6,211,247 B1 4/2001 Goodman
6,217,576 B1 4/2001 Tu et al.
6,219,577 B1 4/2001 Brown, III et al.
6,228,076 B1 5/2001 Winston et al.
6,228,109 B1 5/2001 Tu et al.
6,231,516 B1 5/2001 Keilman et al.
6,231,587 B1 5/2001 Makower
6,235,044 B1 5/2001 Root et al.
6,236,883 B1 5/2001 Ciaccio et al.
6,237,605 B1 5/2001 Vaska et al.
6,238,389 B1 5/2001 Paddock et al.
6,238,392 B1 5/2001 Long
6,241,666 B1 6/2001 Pomeranz et al.
6,241,753 B1 6/2001 Knowlton
6,245,020 B1 6/2001 Moore et al.
6,245,045 B1 6/2001 Stratienko
6,248,126 B1 6/2001 Lesser et al.
6,251,128 B1 6/2001 Knopp et al.
6,258,087 B1 7/2001 Edwards et al.
6,273,886 B1 8/2001 Edwards et al.
6,280,466 B1 8/2001 Kugler et al.
6,283,935 B1 9/2001 Laufer et al.
6,283,959 B1 9/2001 Lalonde et al.
6,284,743 B1 9/2001 Parmacek et al.
6,287,323 B1 9/2001 Hammerslag
6,290,696 B1 9/2001 Lafontaine
6,292,695 B1 9/2001 Webster, Jr. et al.
6,293,942 B1 9/2001 Goble et al.
6,293,943 B1 9/2001 Panescu et al.
6,296,619 B1 10/2001 Brisken et al.
6,298,256 B1 10/2001 Meyer
6,299,379 B1 10/2001 Lewis
6,299,623 B1 10/2001 Wulfman
6,309,379 B1 10/2001 Willard et al.
6,309,399 B1 10/2001 Barbut et al.
6,311,090 B1 10/2001 Knowlton
6,317,615 B1 11/2001 KenKnight et al.
6,319,242 B1 11/2001 Patterson et al.
6,319,251 B1 11/2001 Tu et al.
6,322,559 B1 11/2001 Daulton et al.
6,325,797 B1 12/2001 Stewart et al.
6,325,799 B1 12/2001 Goble
6,328,699 B1 12/2001 Eigler et al.
6,346,074 B1 2/2002 Roth
6,346,104 B2 2/2002 Daly et al.
6,347,247 B1 2/2002 Dev et al.
6,350,248 B1 2/2002 Knudson et al.
6,350,276 B1 2/2002 Knowlton
6,353,751 B1 3/2002 Swanson et al.
6,355,029 B1 3/2002 Joye et al.
6,357,447 B1 3/2002 Swanson et al.
6,361,519 B1 3/2002 Knudson et al.
6,364,840 B1 4/2002 Crowley
6,371,965 B2 4/2002 Gifford, III et al.
6,375,668 B1 4/2002 Gifford et al.
6,377,854 B1 4/2002 Knowlton
6,377,855 B1 4/2002 Knowlton
6,379,352 B1 4/2002 Reynolds et al.
6,379,373 B1 4/2002 Sawhney et al.
6,381,497 B1 4/2002 Knowlton
6,381,498 B1 4/2002 Knowlton
6,383,151 B1 5/2002 Diederich et al.
6,387,105 B1 5/2002 Gifford, III et al.
6,387,380 B1 5/2002 Knowlton
6,389,311 B1 5/2002 Whayne et al.
6,389,314 B2 5/2002 Feiring
6,391,024 B1 5/2002 Sun et al.
6,394,096 B1 5/2002 Constantz
6,394,956 B1 5/2002 Chandrasekaran et al.
6,398,780 B1 6/2002 Farley et al.
6,398,782 B1 6/2002 Pecor et al.
6,398,792 B1 6/2002 O'Connor
6,401,720 B1 6/2002 Stevens et al.
6,402,719 B1 6/2002 Ponzi et al.
6,405,090 B1 6/2002 Knowlton
6,409,723 B1 6/2002 Edwards
6,413,255 B1 7/2002 Stern
6,421,559 B1 7/2002 Pearlman
6,423,057 B1 7/2002 He et al.
6,425,867 B1 7/2002 Vaezy et al.
6,425,912 B1 7/2002 Knowlton
6,427,118 B1 7/2002 Suzuki
6,428,534 B1 8/2002 Joye et al.
6,428,536 B2 8/2002 Panescu et al.
6,430,446 B1 8/2002 Knowlton
6,432,102 B2 8/2002 Joye et al.
6,436,056 B1 8/2002 Wang et al.
6,438,424 B1 8/2002 Knowlton
6,440,125 B1 8/2002 Rentrop
6,442,413 B1 8/2002 Silver
6,443,965 B1 9/2002 Gifford, III et al.
6,445,939 B1 9/2002 Swanson et al.
6,447,505 B2 9/2002 McGovern et al.
6,447,509 B1 9/2002 Bonnet et al.
6,451,034 B1 9/2002 Gifford, III et al.
6,451,044 B1 9/2002 Naghavi et al.
6,453,202 B1 9/2002 Knowlton
6,454,737 B1 9/2002 Nita et al.
6,454,757 B1 9/2002 Nita et al.
6,454,775 B1 9/2002 Demarais et al.
6,458,098 B1 10/2002 Kanesaka
6,461,378 B1 10/2002 Knowlton
6,468,276 B1 10/2002 McKay
6,468,297 B1 10/2002 Williams et al.
6,470,216 B1 10/2002 Knowlton
6,470,219 B1 10/2002 Edwards et al.

(56) References Cited

U.S. PATENT DOCUMENTS

| | | | |
|---|---|---|---|
| 6,471,696 | B1 | 10/2002 | Berube et al. |
| 6,475,213 | B1 | 11/2002 | Whayne et al. |
| 6,475,215 | B1 | 11/2002 | Tanrisever |
| 6,475,238 | B1 | 11/2002 | Fedida et al. |
| 6,477,426 | B1 | 11/2002 | Fenn et al. |
| 6,480,745 | B2 | 11/2002 | Nelson et al. |
| 6,481,704 | B1 | 11/2002 | Koster et al. |
| 6,482,202 | B1 | 11/2002 | Goble et al. |
| 6,484,052 | B1 | 11/2002 | Visuri et al. |
| 6,485,489 | B2 | 11/2002 | Teirstein et al. |
| 6,488,679 | B1 | 12/2002 | Swanson et al. |
| 6,489,307 | B1 | 12/2002 | Phillips et al. |
| 6,491,705 | B2 | 12/2002 | Gifford, III et al. |
| 6,494,891 | B1 | 12/2002 | Cornish et al. |
| 6,497,711 | B1 | 12/2002 | Plaia et al. |
| 6,500,172 | B1 | 12/2002 | Panescu et al. |
| 6,500,174 | B1 | 12/2002 | Maguire et al. |
| 6,508,765 | B2 | 1/2003 | Suorsa et al. |
| 6,508,804 | B2 | 1/2003 | Sarge et al. |
| 6,508,815 | B1 | 1/2003 | Strul et al. |
| 6,511,478 | B1 | 1/2003 | Burnside et al. |
| 6,511,496 | B1 | 1/2003 | Huter et al. |
| 6,511,500 | B1 | 1/2003 | Rahme |
| 6,514,236 | B1 | 2/2003 | Stratienko |
| 6,514,245 | B1 | 2/2003 | Williams et al. |
| 6,514,248 | B1 | 2/2003 | Eggers et al. |
| 6,517,534 | B1 | 2/2003 | McGovern et al. |
| 6,517,572 | B2 | 2/2003 | Kugler et al. |
| 6,522,913 | B2 | 2/2003 | Swanson et al. |
| 6,522,926 | B1 | 2/2003 | Kieval et al. |
| 6,524,299 | B1 | 2/2003 | Tran et al. |
| 6,527,765 | B2 | 3/2003 | Kelman et al. |
| 6,527,769 | B2 | 3/2003 | Langberg et al. |
| 6,540,761 | B2 | 4/2003 | Houser |
| 6,542,781 | B1 | 4/2003 | Koblish et al. |
| 6,544,780 | B1 | 4/2003 | Wang |
| 6,546,272 | B1 | 4/2003 | MacKinnon et al. |
| 6,547,788 | B1 | 4/2003 | Maguire et al. |
| 6,549,800 | B1 | 4/2003 | Atalar et al. |
| 6,552,796 | B2 | 4/2003 | Magnin et al. |
| 6,554,780 | B1 | 4/2003 | Sampson et al. |
| 6,558,381 | B2 | 5/2003 | Ingle et al. |
| 6,558,382 | B2 | 5/2003 | Jahns et al. |
| 6,564,096 | B2 | 5/2003 | Mest |
| 6,565,582 | B2 | 5/2003 | Gifford, III et al. |
| 6,569,109 | B2 | 5/2003 | Sakurai et al. |
| 6,569,177 | B1 | 5/2003 | Dillard et al. |
| 6,570,659 | B2 | 5/2003 | Schmitt |
| 6,571,127 | B1 | 5/2003 | Ben-Haim et al. |
| 6,572,551 | B1 | 6/2003 | Smith et al. |
| 6,572,612 | B2 | 6/2003 | Stewart et al. |
| 6,577,902 | B1 | 6/2003 | Laufer et al. |
| 6,579,308 | B1 | 6/2003 | Jansen et al. |
| 6,579,311 | B1 | 6/2003 | Makower |
| 6,582,423 | B1 | 6/2003 | Thapliyal et al. |
| 6,589,238 | B2 | 7/2003 | Edwards et al. |
| 6,592,526 | B1 | 7/2003 | Lenker |
| 6,592,567 | B1 | 7/2003 | Levin et al. |
| 6,595,959 | B1 | 7/2003 | Stratienko |
| 6,600,956 | B2 | 7/2003 | Maschino et al. |
| 6,602,242 | B1 | 8/2003 | Fung |
| 6,602,246 | B1 | 8/2003 | Joye et al. |
| 6,605,056 | B2 | 8/2003 | Eidenschink et al. |
| 6,605,084 | B2 | 8/2003 | Acker et al. |
| 6,623,452 | B2 | 9/2003 | Chien et al. |
| 6,623,453 | B1 | 9/2003 | Guibert et al. |
| 6,632,193 | B1 | 10/2003 | Davison et al. |
| 6,632,196 | B1 | 10/2003 | Houser |
| 6,645,223 | B2 | 11/2003 | Boyle et al. |
| 6,648,854 | B1 | 11/2003 | Patterson et al. |
| 6,648,878 | B2 | 11/2003 | Lafontaine |
| 6,648,879 | B2 | 11/2003 | Joye et al. |
| 6,651,672 | B2 | 11/2003 | Roth |
| 6,652,513 | B2 | 11/2003 | Panescu et al. |
| 6,652,515 | B1 | 11/2003 | Maguire et al. |
| 6,656,136 | B1 | 12/2003 | Weng et al. |
| 6,658,279 | B2 | 12/2003 | Swanson et al. |
| 6,659,981 | B2 | 12/2003 | Stewart et al. |
| 6,666,858 | B2 | 12/2003 | Lafontaine |
| 6,666,863 | B2 | 12/2003 | Wentzel et al. |
| 6,669,655 | B1 | 12/2003 | Acker et al. |
| 6,669,692 | B1 | 12/2003 | Nelson et al. |
| 6,673,040 | B1 | 1/2004 | Samson et al. |
| 6,673,064 | B1 | 1/2004 | Rentrop |
| 6,673,066 | B2 | 1/2004 | Werneth |
| 6,673,090 | B2 | 1/2004 | Root et al. |
| 6,673,101 | B1 | 1/2004 | Fitzgerald et al. |
| 6,673,290 | B1 | 1/2004 | Whayne et al. |
| 6,676,678 | B2 | 1/2004 | Gifford, III et al. |
| 6,679,268 | B2 | 1/2004 | Stevens et al. |
| 6,681,773 | B2 | 1/2004 | Murphy et al. |
| 6,682,541 | B1 | 1/2004 | Gifford, III et al. |
| 6,684,098 | B2 | 1/2004 | Oshio et al. |
| 6,685,732 | B2 | 2/2004 | Kramer |
| 6,685,733 | B1 | 2/2004 | Dae et al. |
| 6,689,086 | B1 | 2/2004 | Nita et al. |
| 6,689,148 | B2 | 2/2004 | Sawhney et al. |
| 6,690,181 | B1 | 2/2004 | Dowdeswell et al. |
| 6,692,490 | B1 | 2/2004 | Edwards |
| 6,695,830 | B2 | 2/2004 | Vigil et al. |
| 6,695,857 | B2 | 2/2004 | Gifford, III et al. |
| 6,699,241 | B2 | 3/2004 | Rappaport et al. |
| 6,699,257 | B2 | 3/2004 | Gifford, III et al. |
| 6,702,748 | B1 | 3/2004 | Nita et al. |
| 6,702,811 | B2 | 3/2004 | Stewart et al. |
| 6,706,010 | B1 | 3/2004 | Miki et al. |
| 6,706,011 | B1 | 3/2004 | Murphy-Chutorian et al. |
| 6,706,037 | B2 | 3/2004 | Zvuloni et al. |
| 6,709,431 | B2 | 3/2004 | Lafontaine |
| 6,711,429 | B1 | 3/2004 | Gilboa et al. |
| 6,712,815 | B2 | 3/2004 | Sampson et al. |
| 6,714,822 | B2 | 3/2004 | King et al. |
| 6,716,184 | B2 | 4/2004 | Vaezy et al. |
| 6,720,350 | B2 | 4/2004 | Kunz et al. |
| 6,723,043 | B2 | 4/2004 | Kleeman et al. |
| 6,723,064 | B2 | 4/2004 | Babaev |
| 6,736,811 | B2 | 5/2004 | Panescu et al. |
| 6,743,184 | B2 | 6/2004 | Sampson et al. |
| 6,746,401 | B2 | 6/2004 | Panescu |
| 6,746,464 | B1 | 6/2004 | Makower |
| 6,746,474 | B2 | 6/2004 | Saadat |
| 6,748,953 | B2 | 6/2004 | Sherry et al. |
| 6,749,607 | B2 | 6/2004 | Edwards et al. |
| 6,752,805 | B2 | 6/2004 | Maguire et al. |
| 6,760,616 | B2 | 7/2004 | Hoey et al. |
| 6,763,261 | B2 | 7/2004 | Casscells, III et al. |
| 6,764,501 | B2 | 7/2004 | Ganz |
| 6,769,433 | B2 | 8/2004 | Zikorus et al. |
| 6,770,070 | B1 | 8/2004 | Balbierz |
| 6,771,996 | B2 | 8/2004 | Bowe et al. |
| 6,773,433 | B2 | 8/2004 | Stewart et al. |
| 6,786,900 | B2 | 9/2004 | Joye et al. |
| 6,786,901 | B2 | 9/2004 | Joye et al. |
| 6,786,904 | B2 | 9/2004 | Döscher et al. |
| 6,788,977 | B2 | 9/2004 | Fenn et al. |
| 6,790,206 | B2 | 9/2004 | Panescu |
| 6,790,222 | B2 | 9/2004 | Kugler et al. |
| 6,796,981 | B2 | 9/2004 | Wham et al. |
| 6,797,933 | B1 | 9/2004 | Mendis et al. |
| 6,797,960 | B1 | 9/2004 | Spartiotis et al. |
| 6,800,075 | B2 | 10/2004 | Mische et al. |
| 6,802,857 | B1 | 10/2004 | Walsh et al. |
| 6,807,444 | B2 | 10/2004 | Tu et al. |
| 6,810,286 | B2 | 10/2004 | Donovan et al. |
| 6,811,550 | B2 | 11/2004 | Holland et al. |
| 6,813,520 | B2 | 11/2004 | Truckai et al. |
| 6,814,730 | B2 | 11/2004 | Li |
| 6,814,733 | B2 | 11/2004 | Schwartz et al. |
| 6,823,205 | B1 | 11/2004 | Jara |
| 6,824,516 | B2 | 11/2004 | Batten et al. |
| 6,827,726 | B2 | 12/2004 | Parodi |
| 6,827,926 | B2 | 12/2004 | Robinson et al. |
| 6,829,497 | B2 | 12/2004 | Mogul |
| 6,830,568 | B1 | 12/2004 | Kesten et al. |

(56) References Cited

U.S. PATENT DOCUMENTS 6,837,886 B2 1/2005 Collins et al.
6,837,888 B2 1/2005 Ciarrocca et al.
6,845,267 B2 1/2005 Harrison
6,847,848 B2 1/2005 Sterzer
6,849,073 B2 2/2005 Hoey et al.
6,849,075 B2 2/2005 Bertolero et al.
6,853,425 B2 2/2005 Kim et al.
6,855,123 B2 2/2005 Nita
6,855,143 B2 2/2005 Davison
6,865,416 B2 3/2005 Dev et al.
6,869,431 B2 3/2005 Maguire et al.
6,872,183 B2 3/2005 Sampson et al.
6,884,260 B2 4/2005 Kugler et al.
6,889,694 B2 5/2005 Hooven
6,893,436 B2 5/2005 Woodard et al.
6,895,077 B2 5/2005 Karellas et al.
6,895,265 B2 5/2005 Silver
6,898,454 B2 5/2005 Atalar et al.
6,899,711 B2 5/2005 Stewart et al.
6,899,718 B2 5/2005 Gifford, III et al.
6,905,494 B2 6/2005 Yon et al.
6,908,462 B2 6/2005 Joye et al.
6,909,009 B2 6/2005 Koridze
6,911,026 B1 6/2005 Hall et al.
6,915,806 B2 7/2005 Pacek et al.
6,923,805 B1 8/2005 LaFontaine et al.
6,923,808 B2 8/2005 Taimisto
6,926,246 B2 8/2005 Ginggen
6,926,713 B2 8/2005 Rioux et al.
6,926,716 B2 8/2005 Baker et al.
6,929,009 B2 8/2005 Makower et al.
6,929,632 B2 8/2005 Nita et al.
6,929,639 B2 8/2005 Lafontaine
6,932,776 B2 8/2005 Carr
6,936,047 B2 8/2005 Nasab et al.
6,942,620 B2 9/2005 Nita et al.
6,942,657 B2 9/2005 Sinofsky et al.
6,942,677 B2 9/2005 Nita et al.
6,942,692 B2 9/2005 Landau et al.
6,949,097 B2 9/2005 Stewart et al.
6,949,121 B1 9/2005 Laguna
6,952,615 B2 10/2005 Satake
6,953,425 B2 10/2005 Brister
6,955,174 B2 10/2005 Joye et al.
6,955,175 B2 10/2005 Stevens et al.
6,959,711 B2 11/2005 Murphy et al.
6,960,207 B2 11/2005 Vanney et al.
6,962,584 B1 11/2005 Stone et al.
6,964,660 B2 11/2005 Maguire et al.
6,966,908 B2 11/2005 Maguire et al.
6,972,015 B2 12/2005 Joye et al.
6,972,024 B1 12/2005 Kilpatrick et al.
6,974,456 B2 12/2005 Edwards et al.
6,978,174 B2 12/2005 Gelfand et al.
6,979,329 B2 12/2005 Burnside et al.
6,979,420 B2 12/2005 Weber
6,984,238 B2 1/2006 Gifford, III et al.
6,985,774 B2 1/2006 Kieval et al.
6,986,739 B2 1/2006 Warren et al.
6,989,009 B2 1/2006 Lafontaine
6,989,010 B2 1/2006 Francischelli et al.
6,991,617 B2 1/2006 Hektner et al.
7,001,378 B2 2/2006 Yon et al.
7,006,858 B2 2/2006 Silver et al.
7,022,105 B1 4/2006 Edwards
7,022,120 B2 4/2006 Lafontaine
7,025,767 B2 4/2006 Schaefer et al.
7,033,322 B2 4/2006 Silver
7,033,372 B1 4/2006 Cahalan
7,041,098 B2 5/2006 Farley et al.
7,050,848 B2 5/2006 Hoey et al.
7,063,670 B2 6/2006 Sampson et al.
7,063,679 B2 6/2006 Maguire et al.
7,063,719 B2 6/2006 Jansen et al.
7,066,895 B2 6/2006 Podany
7,066,900 B2 6/2006 Botto et al.
7,066,904 B2 6/2006 Rosenthal et al.
7,072,720 B2 7/2006 Puskas
7,074,217 B2 7/2006 Strul et al.
7,081,112 B2 7/2006 Joye et al.
7,081,114 B2 7/2006 Rashidi
7,083,614 B2 8/2006 Fjield et al.
7,084,276 B2 8/2006 Vu et al.
7,087,026 B2 8/2006 Callister et al.
7,087,051 B2 8/2006 Bourne et al.
7,087,052 B2 8/2006 Sampson et al.
7,087,053 B2 8/2006 Vanney
7,089,065 B2 8/2006 Westlund et al.
7,097,641 B1 8/2006 Arless et al.
7,100,614 B2 9/2006 Stevens et al.
7,101,368 B2 9/2006 Lafontaine
7,104,983 B2 9/2006 Grasso, III et al.
7,104,987 B2 9/2006 Biggs et al.
7,108,715 B2 9/2006 Lawrence-Brown et al.
7,112,196 B2 9/2006 Brosch et al.
7,112,198 B2 9/2006 Satake
7,112,211 B2 9/2006 Gifford, III et al.
7,122,019 B1 10/2006 Kesten et al.
7,122,033 B2 10/2006 Wood
7,134,438 B2 11/2006 Makower et al.
7,137,963 B2 11/2006 Nita et al.
7,137,980 B2 11/2006 Buysse et al.
7,153,315 B2 12/2006 Miller
7,155,271 B2 12/2006 Halperin et al.
7,157,491 B2 1/2007 Mewshaw et al.
7,157,492 B2 1/2007 Mewshaw et al.
7,158,832 B2 1/2007 Kieval et al.
7,160,296 B2 1/2007 Pearson et al.
7,162,303 B2 1/2007 Levin et al.
7,165,551 B2 1/2007 Edwards et al.
7,169,144 B2 1/2007 Hoey et al.
7,172,589 B2 2/2007 Lafontaine
7,172,610 B2 2/2007 Heitzmann et al.
7,181,261 B2 2/2007 Silver et al.
7,184,811 B2 2/2007 Phan et al.
7,184,827 B1 2/2007 Edwards
7,189,227 B2 3/2007 Lafontaine
7,192,427 B2 3/2007 Chapelon et al.
7,192,586 B2 3/2007 Bander
7,197,354 B2 3/2007 Sobe
7,198,632 B2 4/2007 Lim et al.
7,200,445 B1 4/2007 Dalbec et al.
7,201,749 B2 4/2007 Govari et al.
7,203,537 B2 4/2007 Mower
7,214,234 B2 5/2007 Rapacki et al.
7,220,233 B2 5/2007 Nita et al.
7,220,239 B2 5/2007 Wilson et al.
7,220,257 B1 5/2007 Lafontaine
7,220,270 B2 5/2007 Sawhney et al.
7,232,458 B2 6/2007 Saadat
7,232,459 B2 6/2007 Greenberg et al.
7,238,184 B2 7/2007 Megerman et al.
7,241,273 B2 7/2007 Maguire et al.
7,241,736 B2 7/2007 Hunter et al.
7,247,141 B2 7/2007 Makin et al.
7,250,041 B2 7/2007 Chiu et al.
7,250,440 B2 7/2007 Mewshaw et al.
7,252,664 B2 8/2007 Nasab et al.
7,252,679 B2 8/2007 Fischell et al.
7,264,619 B2 9/2007 Venturelli
7,279,600 B2 10/2007 Mewshaw et al.
7,280,863 B2 10/2007 Shachar
7,282,213 B2 10/2007 Schroeder et al.
7,285,119 B2 10/2007 Stewart et al.
7,285,120 B2 10/2007 Im et al.
7,288,089 B2 10/2007 Yon et al.
7,288,096 B2 10/2007 Chin
7,291,146 B2 11/2007 Steinke et al.
7,293,562 B2 11/2007 Malecki et al.
7,294,125 B2 11/2007 Phalen et al.
7,294,126 B2 11/2007 Sampson et al.
7,294,127 B2 11/2007 Leung et al.
7,297,131 B2 11/2007 Nita
7,297,475 B2 11/2007 Koiwai et al.

(56) References Cited

U.S. PATENT DOCUMENTS

| | | | |
|---|---|---|---|
| 7,300,433 | B2 | 11/2007 | Lane et al. |
| 7,301,108 | B2 | 11/2007 | Egitto et al. |
| 7,310,150 | B2 | 12/2007 | Guillermo et al. |
| 7,313,430 | B2 | 12/2007 | Urquhart et al. |
| 7,314,480 | B2 | 1/2008 | Eidenschink et al. |
| 7,314,483 | B2 | 1/2008 | Landau et al. |
| 7,317,077 | B2 | 1/2008 | Averback et al. |
| 7,323,006 | B2 | 1/2008 | Andreas et al. |
| 7,326,206 | B2 | 2/2008 | Paul et al. |
| 7,326,226 | B2 | 2/2008 | Root et al. |
| 7,326,235 | B2 | 2/2008 | Edwards |
| 7,326,237 | B2 | 2/2008 | DePalma et al. |
| 7,329,236 | B2 | 2/2008 | Kesten et al. |
| 7,335,180 | B2 | 2/2008 | Nita et al. |
| 7,335,192 | B2 | 2/2008 | Keren et al. |
| 7,338,467 | B2 | 3/2008 | Lutter |
| 7,341,570 | B2 | 3/2008 | Keren et al. |
| 7,343,195 | B2 | 3/2008 | Strommer et al. |
| 7,347,857 | B2 | 3/2008 | Anderson et al. |
| 7,348,003 | B2 | 3/2008 | Salcedo et al. |
| 7,352,593 | B2 | 4/2008 | Zeng et al. |
| 7,354,927 | B2 | 4/2008 | Vu |
| 7,359,732 | B2 | 4/2008 | Kim et al. |
| 7,361,341 | B2 | 4/2008 | Salcedo et al. |
| 7,364,566 | B2 | 4/2008 | Elkins et al. |
| 7,367,970 | B2 | 5/2008 | Govari et al. |
| 7,367,975 | B2 | 5/2008 | Malecki et al. |
| 7,371,231 | B2 | 5/2008 | Rioux et al. |
| 7,387,126 | B2 | 6/2008 | Cox et al. |
| 7,393,338 | B2 | 7/2008 | Nita |
| 7,396,355 | B2 | 7/2008 | Goldman et al. |
| 7,402,151 | B2 | 7/2008 | Rosenman et al. |
| 7,402,312 | B2 | 7/2008 | Rosen et al. |
| 7,404,824 | B1 | 7/2008 | Webler et al. |
| 7,406,970 | B2 | 8/2008 | Zikorus et al. |
| 7,407,502 | B2 | 8/2008 | Strul et al. |
| 7,407,506 | B2 | 8/2008 | Makower |
| 7,407,671 | B2 | 8/2008 | McBride et al. |
| 7,408,021 | B2 | 8/2008 | Averback et al. |
| 7,410,486 | B2 | 8/2008 | Fuimaono et al. |
| 7,413,556 | B2 | 8/2008 | Zhang et al. |
| 7,425,212 | B1 | 9/2008 | Danek et al. |
| 7,426,409 | B2 | 9/2008 | Casscells, III et al. |
| 7,435,248 | B2 | 10/2008 | Taimisto et al. |
| 7,447,453 | B2 | 11/2008 | Kim et al. |
| 7,449,018 | B2 | 11/2008 | Kramer |
| 7,452,538 | B2 | 11/2008 | Ni et al. |
| 7,473,890 | B2 | 1/2009 | Grier et al. |
| 7,476,384 | B2 | 1/2009 | Ni et al. |
| 7,479,157 | B2 | 1/2009 | Weber et al. |
| 7,481,803 | B2 | 1/2009 | Kesten et al. |
| 7,485,104 | B2 | 2/2009 | Kieval |
| 7,486,805 | B2 | 2/2009 | Krattiger |
| 7,487,780 | B2 | 2/2009 | Hooven |
| 7,493,154 | B2 | 2/2009 | Bonner et al. |
| 7,494,485 | B2 | 2/2009 | Beck et al. |
| 7,494,486 | B2 | 2/2009 | Mische et al. |
| 7,494,488 | B2 | 2/2009 | Weber |
| 7,494,661 | B2 | 2/2009 | Sanders |
| 7,495,439 | B2 | 2/2009 | Wiggins |
| 7,497,858 | B2 | 3/2009 | Chapelon et al. |
| 7,499,745 | B2 | 3/2009 | Littrup et al. |
| 7,500,985 | B2 | 3/2009 | Saadat |
| 7,505,812 | B1 | 3/2009 | Eggers et al. |
| 7,505,816 | B2 | 3/2009 | Schmeling et al. |
| 7,507,233 | B2 | 3/2009 | Littrup et al. |
| 7,507,235 | B2 | 3/2009 | Keogh et al. |
| 7,511,494 | B2 | 3/2009 | Wedeen |
| 7,512,445 | B2 | 3/2009 | Truckai et al. |
| 7,527,643 | B2 | 5/2009 | Case et al. |
| 7,529,589 | B2 | 5/2009 | Williams et al. |
| 7,540,852 | B2 | 6/2009 | Nita et al. |
| 7,540,870 | B2 | 6/2009 | Babaev |
| RE40,863 | E | 7/2009 | Tay et al. |
| 7,556,624 | B2 | 7/2009 | Laufer et al. |
| 7,558,625 | B2 | 7/2009 | Levin et al. |
| 7,563,247 | B2 | 7/2009 | Maguire et al. |
| 7,566,319 | B2 | 7/2009 | McAuley et al. |
| 7,569,052 | B2 | 8/2009 | Phan et al. |
| 7,582,111 | B2 | 9/2009 | Krolik et al. |
| 7,584,004 | B2 | 9/2009 | Caparso et al. |
| 7,585,835 | B2 | 9/2009 | Hill et al. |
| 7,591,996 | B2 | 9/2009 | Hwang et al. |
| 7,597,704 | B2 | 10/2009 | Frazier et al. |
| 7,598,228 | B2 | 10/2009 | Hattori et al. |
| 7,599,730 | B2 | 10/2009 | Hunter et al. |
| 7,603,166 | B2 | 10/2009 | Casscells, III et al. |
| 7,604,608 | B2 | 10/2009 | Nita et al. |
| 7,604,633 | B2 | 10/2009 | Truckai et al. |
| 7,615,015 | B2 | 11/2009 | Coleman |
| 7,615,072 | B2 | 11/2009 | Rust et al. |
| 7,617,005 | B2 | 11/2009 | Demarais et al. |
| 7,620,451 | B2 | 11/2009 | Demarais et al. |
| 7,621,902 | B2 | 11/2009 | Nita et al. |
| 7,621,929 | B2 | 11/2009 | Nita et al. |
| 7,626,015 | B2 | 12/2009 | Feinstein et al. |
| 7,626,235 | B2 | 12/2009 | Kinoshita |
| 7,632,268 | B2 | 12/2009 | Edwards et al. |
| 7,632,845 | B2 | 12/2009 | Vu et al. |
| 7,635,383 | B2 | 12/2009 | Gumm |
| 7,640,046 | B2 | 12/2009 | Pastore et al. |
| 7,641,633 | B2 | 1/2010 | Laufer et al. |
| 7,641,679 | B2 | 1/2010 | Joye et al. |
| 7,646,544 | B2 | 1/2010 | Batchko et al. |
| 7,647,115 | B2 | 1/2010 | Levin et al. |
| 7,653,438 | B2 | 1/2010 | Deem et al. |
| 7,655,006 | B2 | 2/2010 | Sauvageau et al. |
| 7,662,114 | B2 | 2/2010 | Seip et al. |
| 7,664,548 | B2 | 2/2010 | Amurthur et al. |
| 7,670,279 | B2 | 3/2010 | Gertner |
| 7,670,335 | B2 | 3/2010 | Keidar |
| 7,671,084 | B2 | 3/2010 | Mewshaw et al. |
| 7,678,104 | B2 | 3/2010 | Keidar |
| 7,678,106 | B2 | 3/2010 | Lee |
| 7,678,108 | B2 | 3/2010 | Chrisitian et al. |
| 7,686,841 | B2 | 3/2010 | Eidenschink et al. |
| 7,691,080 | B2 | 4/2010 | Seward et al. |
| 7,699,809 | B2 | 4/2010 | Urmey |
| 7,706,882 | B2 | 4/2010 | Francischelli et al. |
| 7,715,912 | B2 | 5/2010 | Rezai et al. |
| 7,717,853 | B2 | 5/2010 | Nita |
| 7,717,909 | B2 | 5/2010 | Strul et al. |
| 7,717,948 | B2 | 5/2010 | Demarais et al. |
| 7,722,539 | B2 | 5/2010 | Carter et al. |
| 7,725,157 | B2 | 5/2010 | Dumoulin et al. |
| 7,727,178 | B2 | 6/2010 | Wilson et al. |
| 7,736,317 | B2 | 6/2010 | Stephens et al. |
| 7,736,360 | B2 | 6/2010 | Mody et al. |
| 7,736,362 | B2 | 6/2010 | Eberl et al. |
| 7,738,952 | B2 | 6/2010 | Yun et al. |
| 7,740,629 | B2 | 6/2010 | Anderson et al. |
| 7,741,299 | B2 | 6/2010 | Feinstein et al. |
| 7,742,795 | B2 | 6/2010 | Stone et al. |
| 7,744,594 | B2 | 6/2010 | Yamazaki et al. |
| 7,753,907 | B2 | 7/2010 | DiMatteo et al. |
| 7,756,583 | B2 | 7/2010 | Demarais et al. |
| 7,758,510 | B2 | 7/2010 | Nita et al. |
| 7,758,520 | B2 | 7/2010 | Griffin et al. |
| 7,759,315 | B2 | 7/2010 | Cuzzocrea et al. |
| 7,766,833 | B2 | 8/2010 | Lee et al. |
| 7,766,878 | B2 | 8/2010 | Tremaglio, Jr. et al. |
| 7,766,892 | B2 | 8/2010 | Keren et al. |
| 7,767,844 | B2 | 8/2010 | Lee et al. |
| 7,769,427 | B2 | 8/2010 | Shachar |
| 7,771,372 | B2 | 8/2010 | Wilson |
| 7,771,421 | B2 | 8/2010 | Stewart et al. |
| 7,776,967 | B2 | 8/2010 | Perry et al. |
| 7,777,486 | B2 | 8/2010 | Hargreaves et al. |
| 7,780,660 | B2 | 8/2010 | Bourne et al. |
| 7,789,876 | B2 | 9/2010 | Zikorus et al. |
| 7,792,568 | B2 | 9/2010 | Zhong et al. |
| 7,799,021 | B2 | 9/2010 | Leung et al. |
| 7,803,168 | B2 | 9/2010 | Gifford et al. |
| 7,806,871 | B2 | 10/2010 | Li et al. |

(56) References Cited

U.S. PATENT DOCUMENTS 7,811,265 B2 10/2010 Hering et al.
7,811,281 B1 10/2010 Rentrop
7,811,313 B2 10/2010 Mon et al.
7,816,511 B2 10/2010 Kawashima et al.
7,818,053 B2 10/2010 Kassab
7,819,866 B2 10/2010 Bednarek
7,822,460 B2 10/2010 Halperin et al.
7,828,837 B2 11/2010 Khoury
7,832,407 B2 11/2010 Gertner
7,833,220 B2 11/2010 Mon et al.
7,837,676 B2 11/2010 Sinelnikov et al.
7,837,720 B2 11/2010 Mon
7,841,978 B2 11/2010 Gertner
7,846,157 B2 12/2010 Kozel
7,846,160 B2 12/2010 Payne et al.
7,846,172 B2 12/2010 Makower
7,849,860 B2 12/2010 Makower et al.
7,850,685 B2 12/2010 Kunis et al.
7,853,333 B2 12/2010 Demarais
7,854,734 B2 12/2010 Biggs et al.
7,857,756 B2 12/2010 Warren et al.
7,862,565 B2 1/2011 Eder et al.
7,863,897 B2 1/2011 Slocum, Jr. et al.
7,869,854 B2 1/2011 Shachar et al.
7,873,417 B2 1/2011 Demarais et al.
7,887,538 B2 2/2011 Bleich et al.
7,894,905 B2 2/2011 Pless et al.
7,896,873 B2 3/2011 Hiller et al.
7,901,400 B2 3/2011 Wham et al.
7,901,402 B2 3/2011 Jones et al.
7,901,420 B2 3/2011 Dunn
7,905,862 B2 3/2011 Sampson
7,918,850 B2 4/2011 Govari et al.
7,927,370 B2 4/2011 Webler et al.
7,937,143 B2 5/2011 Demarais et al.
7,938,830 B2 5/2011 Saadat et al.
7,942,874 B2 5/2011 Eder et al.
7,942,928 B2 5/2011 Webler et al.
7,946,976 B2 5/2011 Gertner
7,950,397 B2 5/2011 Thapliyal et al.
7,955,293 B2 6/2011 Nita et al.
7,956,613 B2 6/2011 Wald
7,959,627 B2 6/2011 Utley et al.
7,962,854 B2 6/2011 Vance et al.
7,967,782 B2 6/2011 Laufer et al.
7,967,808 B2 6/2011 Fitzgerald et al.
7,972,327 B2 7/2011 Eberl et al.
7,972,330 B2 7/2011 Alejandro et al.
7,983,751 B2 7/2011 Zdeblick et al.
8,001,976 B2 8/2011 Gertner
8,007,440 B2 8/2011 Magnin et al.
8,012,147 B2 9/2011 Lafontaine
8,019,435 B2 * 9/2011 Hastings et al. .............. 607/115
8,021,362 B2 9/2011 Deem et al.
8,021,413 B2 9/2011 Dierking et al.
8,025,661 B2 9/2011 Arnold et al.
8,027,718 B2 9/2011 Spinner et al.
8,031,927 B2 10/2011 Karl et al.
8,033,284 B2 10/2011 Porter et al.
8,043,673 B2 10/2011 Lee et al.
8,048,144 B2 11/2011 Thistle et al.
8,052,636 B2 11/2011 Moll et al.
8,052,700 B2 11/2011 Dunn
8,062,289 B2 11/2011 Babaev
8,075,580 B2 12/2011 Makower
8,080,006 B2 12/2011 Lafontaine et al.
8,088,127 B2 1/2012 Mayse et al.
8,116,883 B2 2/2012 Williams et al.
8,119,183 B2 2/2012 O'Donoghue et al.
8,120,518 B2 2/2012 Jang et al.
8,123,741 B2 2/2012 Marrouche et al.
8,128,617 B2 3/2012 Bencini et al.
8,131,371 B2 3/2012 Demarals et al.
8,131,372 B2 3/2012 Levin et al.
8,131,382 B2 3/2012 Asada
8,137,274 B2 3/2012 Weng et al.
8,140,170 B2 3/2012 Rezai et al.
8,143,316 B2 3/2012 Ueno
8,145,316 B2 3/2012 Deem et al.
8,145,317 B2 3/2012 Demarais et al.
8,150,518 B2 4/2012 Levin et al.
8,150,519 B2 4/2012 Demarais et al.
8,150,520 B2 4/2012 Demarais et al.
8,152,830 B2 4/2012 Gumm
8,162,933 B2 4/2012 Francischelli et al.
8,168,275 B2 5/2012 Lee et al.
8,175,711 B2 5/2012 Demarais et al.
8,187,261 B2 5/2012 Watson
8,190,238 B2 5/2012 Moll et al.
8,192,053 B2 6/2012 Owen et al.
8,198,611 B2 6/2012 LaFontaine et al.
8,214,056 B2 7/2012 Hoffer et al.
8,221,407 B2 7/2012 Phan et al.
8,226,637 B2 7/2012 Satake
8,231,617 B2 7/2012 Satake
8,241,217 B2 8/2012 Chiang et al.
8,257,724 B2 9/2012 Cromack et al.
8,257,725 B2 9/2012 Cromack et al.
8,260,397 B2 9/2012 Ruff et al.
8,263,104 B2 9/2012 Ho et al.
8,273,023 B2 9/2012 Razavi
8,277,379 B2 10/2012 Lau et al.
8,287,524 B2 10/2012 Siegel
8,287,532 B2 10/2012 Carroll et al.
8,292,881 B2 10/2012 Brannan et al.
8,293,703 B2 10/2012 Averback et al.
8,295,902 B2 10/2012 Salahieh et al.
8,295,912 B2 10/2012 Gertner
8,308,722 B2 11/2012 Ormsby et al.
8,317,776 B2 11/2012 Ferren et al.
8,317,810 B2 11/2012 Stangenes et al.
8,329,179 B2 12/2012 Ni et al.
8,336,705 B2 12/2012 Okahisa
8,343,031 B2 1/2013 Gertner
8,343,145 B2 1/2013 Brannan
8,347,891 B2 1/2013 Demarais et al.
8,353,945 B2 1/2013 Andreas et al.
8,364,237 B2 1/2013 Stone et al.
8,366,615 B2 2/2013 Razavi
8,382,697 B2 2/2013 Brenneman et al.
8,388,680 B2 3/2013 Starksen et al.
8,391,971 B2 * 3/2013 Hastings et al. .................. 607/2
8,396,548 B2 3/2013 Perry et al.
8,398,629 B2 3/2013 Thistle
8,401,667 B2 3/2013 Gustus et al.
8,403,881 B2 3/2013 Ferren et al.
8,406,877 B2 3/2013 Smith et al.
8,409,172 B2 4/2013 Moll et al.
8,409,193 B2 4/2013 Young et al.
8,409,195 B2 4/2013 Young
8,418,362 B2 4/2013 Zerfas et al.
8,452,988 B2 5/2013 Wang
8,454,594 B2 6/2013 Demarais et al.
8,460,358 B2 6/2013 Andreas et al.
8,465,452 B2 6/2013 Kassab
8,469,919 B2 6/2013 Ingle et al.
8,473,067 B2 6/2013 Hastings et al.
8,480,663 B2 7/2013 Ingle et al.
8,485,992 B2 7/2013 Griffin et al.
8,486,060 B2 7/2013 Kotmel et al.
8,486,063 B2 7/2013 Werneth et al.
8,488,591 B2 7/2013 Miali et al.
2001/0007070 A1 7/2001 Stewart et al.
2001/0039419 A1 11/2001 Francischelli et al.
2002/0010461 A1 1/2002 Kenknight et al.
2002/0022864 A1 2/2002 Mahvi et al.
2002/0042639 A1 4/2002 Murphy-Chutorian et al.
2002/0045811 A1 4/2002 Kittrell et al.
2002/0045890 A1 4/2002 Celliers et al.
2002/0062146 A1 5/2002 Makower et al.
2002/0065542 A1 5/2002 Lax et al.
2002/0087151 A1 7/2002 Mody et al.
2002/0095197 A1 7/2002 Lardo et al.
2002/0107536 A1 8/2002 Hussein

(56) References Cited

U.S. PATENT DOCUMENTS

2002/0147480 A1 10/2002 Mamayek
2002/0169444 A1 11/2002 Mest et al.
2002/0198520 A1 12/2002 Coen et al.
2003/0050635 A1 3/2003 Truckai et al.
2003/0055465 A1 3/2003 Ben-Haim et al.
2003/0065317 A1 4/2003 Rudie et al.
2003/0092995 A1 5/2003 Thompson
2003/0139689 A1 7/2003 Shturman et al.
2003/0167081 A1* 9/2003 Zhu et al. .................... 607/122
2003/0187340 A1 10/2003 KenKnight et al.
2003/0195501 A1 10/2003 Sherman et al.
2003/0199747 A1 10/2003 Michlitsch et al.
2003/0216792 A1* 11/2003 Levin et al. .................... 607/48
2003/0229340 A1 12/2003 Sherry et al.
2003/0233099 A1 12/2003 Danaek et al.
2004/0010118 A1 1/2004 Zerhusen et al.
2004/0019348 A1 1/2004 Stevens et al.
2004/0024371 A1 2/2004 Plicchi et al.
2004/0043030 A1 3/2004 Griffiths et al.
2004/0064090 A1 4/2004 Keren et al.
2004/0073206 A1 4/2004 Foley et al.
2004/0088002 A1 5/2004 Boyle et al.
2004/0093055 A1 5/2004 Bartorelli et al.
2004/0106871 A1 6/2004 Hunyor et al.
2004/0117032 A1 6/2004 Roth
2004/0147915 A1 7/2004 Hasebe
2004/0162555 A1 8/2004 Farley et al.
2004/0167506 A1 8/2004 Chen
2004/0186356 A1 9/2004 O'Malley et al.
2004/0186546 A1 9/2004 Mandrusov et al.
2004/0187875 A1 9/2004 He et al.
2004/0193211 A1 9/2004 Voegele et al.
2004/0220556 A1 11/2004 Cooper et al.
2004/0243022 A1 12/2004 Carney et al.
2004/0253304 A1 12/2004 Gross et al.
2004/0267250 A1 12/2004 Yon et al.
2005/0010095 A1 1/2005 Stewart et al.
2005/0015125 A1 1/2005 Mioduski et al.
2005/0080374 A1 4/2005 Esch et al.
2005/0096647 A1 5/2005 Steinke et al.
2005/0101697 A1 5/2005 Morihiro et al.
2005/0129616 A1 6/2005 Salcedo et al.
2005/0137180 A1 6/2005 Robinson et al.
2005/0143817 A1 6/2005 Hunter et al.
2005/0148842 A1 7/2005 Wang et al.
2005/0149069 A1 7/2005 Bertolero et al.
2005/0149080 A1 7/2005 Hunter et al.
2005/0149158 A1 7/2005 Hunter et al.
2005/0149173 A1 7/2005 Hunter et al.
2005/0149175 A1 7/2005 Hunter et al.
2005/0154277 A1 7/2005 Tang et al.
2005/0154445 A1 7/2005 Hunter et al.
2005/0154453 A1 7/2005 Hunter et al.
2005/0154454 A1 7/2005 Hunter et al.
2005/0165389 A1 7/2005 Swain et al.
2005/0165391 A1 7/2005 Maguire et al.
2005/0165467 A1 7/2005 Hunter et al.
2005/0165488 A1 7/2005 Hunter et al.
2005/0171575 A1 8/2005 Dev et al.
2005/0175661 A1 8/2005 Hunter et al.
2005/0175662 A1 8/2005 Hunter et al.
2005/0175663 A1 8/2005 Hunter et al.
2005/0177103 A1 8/2005 Hunter et al.
2005/0177225 A1 8/2005 Hunter et al.
2005/0181004 A1 8/2005 Hunter et al.
2005/0181008 A1 8/2005 Hunter et al.
2005/0181011 A1 8/2005 Hunter et al.
2005/0181977 A1 8/2005 Hunter et al.
2005/0182479 A1 8/2005 Bonsignore et al.
2005/0183728 A1 8/2005 Hunter et al.
2005/0186242 A1 8/2005 Hunter et al.
2005/0186243 A1 8/2005 Hunter et al.
2005/0191331 A1 9/2005 Hunter et al.
2005/0203410 A1 9/2005 Jenkins
2005/0209587 A1 9/2005 Joye et al.
2005/0214205 A1 9/2005 Salcedo et al.
2005/0214207 A1 9/2005 Salcedo et al.
2005/0214208 A1 9/2005 Salcedo et al.
2005/0214209 A1 9/2005 Salcedo et al.
2005/0214210 A1 9/2005 Salcedo et al.
2005/0214268 A1 9/2005 Cavanagh et al.
2005/0228286 A1 10/2005 Messerly et al.
2005/0228415 A1 10/2005 Gertner
2005/0228460 A1 10/2005 Levin et al.
2005/0232921 A1 10/2005 Rosen et al.
2005/0234312 A1 10/2005 Suzuki et al.
2005/0245862 A1 11/2005 Seward
2005/0251116 A1 11/2005 Steinke et al.
2005/0252553 A1 11/2005 Ginggen
2005/0256398 A1 11/2005 Hastings et al.
2005/0267556 A1 12/2005 Shuros et al.
2005/0273149 A1 12/2005 Tran et al.
2006/0004323 A1 1/2006 Chang et al.
2006/0018949 A1 1/2006 Ammon et al.
2006/0024564 A1 2/2006 Manclaw
2006/0025765 A1 2/2006 Landman et al.
2006/0030887 A1 2/2006 Letort et al.
2006/0062786 A1 3/2006 Salcedo et al.
2006/0083194 A1 4/2006 Dhrimaj et al.
2006/0085054 A1 4/2006 Zikorus et al.
2006/0089637 A1 4/2006 Werneth et al.
2006/0089638 A1 4/2006 Carmel et al.
2006/0095096 A1 5/2006 DeBenedictis et al.
2006/0106375 A1 5/2006 Werneth et al.
2006/0142790 A1 6/2006 Gertner
2006/0142801 A1 6/2006 Demarais et al.
2006/0147492 A1 7/2006 Hunter et al.
2006/0167106 A1 7/2006 Zhang et al.
2006/0167498 A1 7/2006 DiLorenzo
2006/0171895 A1 8/2006 Bucay-Couto
2006/0182873 A1 8/2006 Klisch et al.
2006/0184221 A1 8/2006 Stewart et al.
2006/0195139 A1 8/2006 Gertner
2006/0206150 A1 9/2006 Demarais et al.
2006/0224153 A1 10/2006 Fischell et al.
2006/0229677 A1* 10/2006 Moffitt et al. .................... 607/2
2006/0239921 A1 10/2006 Mangat et al.
2006/0240070 A1 10/2006 Cromack et al.
2006/0247266 A1 11/2006 Yamada et al.
2006/0247760 A1 11/2006 Ganesan et al.
2006/0263393 A1 11/2006 Demopulos et al.
2006/0269555 A1 11/2006 Salcedo et al.
2006/0271111 A1 11/2006 Demarais et al.
2006/0287644 A1 12/2006 Inganas et al.
2007/0016184 A1 1/2007 Cropper et al.
2007/0016274 A1 1/2007 Boveja et al.
2007/0027390 A1 2/2007 Maschke et al.
2007/0043077 A1 2/2007 Mewshaw et al.
2007/0043409 A1 2/2007 Brian et al.
2007/0049924 A1 3/2007 Rahn
2007/0066972 A1 3/2007 Ormsby et al.
2007/0067883 A1 3/2007 Sretavan
2007/0073151 A1 3/2007 Lee
2007/0093710 A1 4/2007 Maschke
2007/0100405 A1 5/2007 Thompson et al.
2007/0106247 A1 5/2007 Burnett et al.
2007/0112327 A1 5/2007 Yun et al.
2007/0118107 A1 5/2007 Francischelli et al.
2007/0129720 A1 6/2007 Demarais et al.
2007/0129760 A1 6/2007 Demarais et al.
2007/0129761 A1 6/2007 Demarais et al.
2007/0135875 A1 6/2007 Demarais et al.
2007/0149963 A1 6/2007 Matsukuma et al.
2007/0162109 A1 7/2007 Davila et al.
2007/0173805 A1 7/2007 Weinberg et al.
2007/0179496 A1 8/2007 Swoyer et al.
2007/0191904 A1* 8/2007 Libbus et al. .................... 607/44
2007/0203480 A1 8/2007 Mody et al.
2007/0207186 A1 9/2007 Scanlon et al.
2007/0208134 A1 9/2007 Hunter et al.
2007/0208210 A1 9/2007 Gelfand et al.
2007/0208256 A1 9/2007 Marilla
2007/0208301 A1 9/2007 Evard et al.
2007/0219576 A1 9/2007 Cangialosi

(56) References Cited

U.S. PATENT DOCUMENTS

2007/0225781 A1 9/2007 Saadat et al.
2007/0233170 A1 10/2007 Gertner
2007/0239062 A1 10/2007 Chopra et al.
2007/0248639 A1 10/2007 Demopulos et al.
2007/0249703 A1 10/2007 Mewshaw et al.
2007/0254833 A1 11/2007 Hunter et al.
2007/0265687 A1 11/2007 Deem et al.
2007/0278103 A1 12/2007 Hoerr et al.
2007/0282302 A1 12/2007 Wachsman et al.
2007/0292411 A1 12/2007 Salcedo et al.
2007/0293782 A1 12/2007 Marino
2007/0299043 A1 12/2007 Hunter et al.
2008/0004673 A1 1/2008 Rossing et al.
2008/0009927 A1 1/2008 Vilims
2008/0015501 A1 1/2008 Gertner
2008/0021408 A1 1/2008 Jacobsen et al.
2008/0033049 A1 2/2008 Mewshaw
2008/0039746 A1 2/2008 Hissong et al.
2008/0039830 A1 2/2008 Munger et al.
2008/0051454 A1 2/2008 Wang
2008/0064957 A1 3/2008 Spence
2008/0071269 A1 3/2008 Hilario et al.
2008/0071306 A1 3/2008 Gertner
2008/0082109 A1 4/2008 Moll et al.
2008/0086072 A1 4/2008 Bonutti et al.
2008/0091193 A1 4/2008 Kauphusman et al.
2008/0097251 A1 4/2008 Babaev
2008/0097426 A1 4/2008 Root et al.
2008/0108867 A1 5/2008 Zhou
2008/0119879 A1 5/2008 Brenneman et al.
2008/0125772 A1 5/2008 Stone et al.
2008/0132450 A1 6/2008 Lee et al.
2008/0140002 A1 6/2008 Ramzipoor et al.
2008/0147002 A1 6/2008 Gertner
2008/0161662 A1 7/2008 Golijanin et al.
2008/0161717 A1 7/2008 Gertner
2008/0161801 A1 7/2008 Steinke et al.
2008/0171974 A1 7/2008 Lafontaine et al.
2008/0172035 A1 7/2008 Starksen et al.
2008/0172104 A1 7/2008 Kieval et al.
2008/0188912 A1 8/2008 Stone et al.
2008/0188913 A1 8/2008 Stone et al.
2008/0208162 A1 8/2008 Joshi
2008/0208169 A1 8/2008 Boyle et al.
2008/0213331 A1 9/2008 Gelfand et al.
2008/0215117 A1 9/2008 Gross
2008/0221448 A1 9/2008 Khuri-Yakub et al.
2008/0234790 A1 9/2008 Bayer et al.
2008/0243091 A1 10/2008 Humphreys et al.
2008/0245371 A1 10/2008 Gruber
2008/0249525 A1 10/2008 Lee et al.
2008/0249547 A1 10/2008 Dunn
2008/0255550 A1 10/2008 Bell
2008/0255642 A1 10/2008 Zarins et al.
2008/0262489 A1 10/2008 Steinke
2008/0275484 A1 11/2008 Gertner
2008/0281312 A1 11/2008 Werneth et al.
2008/0281347 A1 11/2008 Gertner
2008/0287918 A1 11/2008 Rosenman et al.
2008/0294037 A1 11/2008 Richter
2008/0300618 A1 12/2008 Gertner
2008/0312644 A1 12/2008 Fourkas et al.
2008/0312673 A1 12/2008 Viswanathan et al.
2008/0317818 A1 12/2008 Griffith et al.
2009/0018486 A1 1/2009 Goren et al.
2009/0018609 A1 1/2009 DiLorenzo
2009/0024194 A1 1/2009 Arcot-Krishnamurthy et al.
2009/0030312 A1 1/2009 Hadjicostis
2009/0036948 A1 2/2009 Levin et al.
2009/0043372 A1 2/2009 Northrop et al.
2009/0054082 A1 2/2009 Kim et al.
2009/0062873 A1 3/2009 Wu et al.
2009/0069671 A1 3/2009 Anderson
2009/0076409 A1 3/2009 Wu et al.
2009/0088735 A1 4/2009 Abboud et al.
2009/0105631 A1 4/2009 Kieval
2009/0112202 A1 4/2009 Young
2009/0118620 A1 5/2009 Tgavalekos et al.
2009/0118726 A1 5/2009 Auth et al.
2009/0125099 A1 5/2009 Weber et al.
2009/0131798 A1 5/2009 Minar et al.
2009/0143640 A1 6/2009 Saadat et al.
2009/0156988 A1 6/2009 Ferren et al.
2009/0157057 A1 6/2009 Ferren et al.
2009/0157161 A1 6/2009 Desai et al.
2009/0171333 A1 7/2009 Hon
2009/0192558 A1 7/2009 Whitehurst et al.
2009/0198223 A1 8/2009 Thilwind et al.
2009/0203962 A1 8/2009 Miller et al.
2009/0203993 A1 8/2009 Mangat et al.
2009/0204170 A1 8/2009 Hastings et al.
2009/0210953 A1 8/2009 Moyer et al.
2009/0216317 A1 8/2009 Cromack et al.
2009/0221955 A1 9/2009 Babaev
2009/0226429 A1 9/2009 Salcedo et al.
2009/0240249 A1 9/2009 Chan et al.
2009/0247933 A1 10/2009 Maor et al.
2009/0247966 A1 10/2009 Gunn et al.
2009/0248012 A1 10/2009 Maor et al.
2009/0253974 A1 10/2009 Rahme
2009/0264755 A1 10/2009 Chen et al.
2009/0270850 A1 10/2009 Zhou et al.
2009/0281533 A1 11/2009 Ingle et al.
2009/0287137 A1 11/2009 Crowley
2009/0318749 A1 12/2009 Stolen et al.
2010/0009267 A1 1/2010 Chase et al.
2010/0030061 A1 2/2010 Canfield et al.
2010/0048983 A1 2/2010 Ball et al.
2010/0049099 A1 2/2010 Thapliyal et al.
2010/0049186 A1 2/2010 Ingle et al.
2010/0049188 A1 2/2010 Nelson et al.
2010/0049191 A1 2/2010 Habib et al.
2010/0049283 A1 2/2010 Johnson
2010/0069837 A1 3/2010 Rassat et al.
2010/0076299 A1 3/2010 Gustus et al.
2010/0076425 A1 3/2010 Carroux
2010/0087782 A1 4/2010 Ghaffari et al.
2010/0106005 A1 4/2010 Karczmar et al.
2010/0114244 A1 5/2010 Manda et al.
2010/0130836 A1 5/2010 Malchano et al.
2010/0137860 A1 6/2010 Demarais et al.
2010/0137952 A1 6/2010 Demarais et al.
2010/0160903 A1 6/2010 Krespi
2010/0160906 A1 6/2010 Jarrard
2010/0168624 A1 7/2010 Sliwa
2010/0168731 A1 7/2010 Wu et al.
2010/0168739 A1 7/2010 Wu et al.
2010/0174282 A1 7/2010 Demarais et al.
2010/0191112 A1 7/2010 Demarais et al.
2010/0191232 A1 7/2010 Boveda
2010/0217162 A1 8/2010 Hissong et al.
2010/0222786 A1 9/2010 Kassab
2010/0222851 A1 9/2010 Deem et al.
2010/0222854 A1 9/2010 Demarais et al.
2010/0228122 A1 9/2010 Keenan et al.
2010/0249604 A1 9/2010 Hastings et al.
2010/0249773 A1 9/2010 Clark et al.
2010/0256616 A1 10/2010 Katoh et al.
2010/0268217 A1 10/2010 Habib
2010/0268307 A1 10/2010 Demarais et al.
2010/0284927 A1 11/2010 Lu et al.
2010/0286684 A1 11/2010 Hata et al.
2010/0298821 A1 11/2010 Garbagnati
2010/0305036 A1 12/2010 Barnes et al.
2010/0312141 A1 12/2010 Keast et al.
2010/0324472 A1 12/2010 Wulfman
2011/0009750 A1 1/2011 Taylor et al.
2011/0021976 A1 1/2011 Li et al.
2011/0034832 A1 2/2011 Cioanta et al.
2011/0040324 A1 2/2011 McCarthy et al.
2011/0044942 A1 2/2011 Puri et al.
2011/0060324 A1 3/2011 Wu et al.
2011/0071400 A1 3/2011 Hastings et al.
2011/0071401 A1 3/2011 Hastings et al.

(56) References Cited

U.S. PATENT DOCUMENTS

| | | | |
|---|---|---|---|
| 2011/0077498 | A1 | 3/2011 | McDaniel |
| 2011/0092781 | A1 | 4/2011 | Gertner |
| 2011/0092880 | A1 | 4/2011 | Gertner |
| 2011/0104061 | A1 | 5/2011 | Seward |
| 2011/0112400 | A1 | 5/2011 | Emery et al. |
| 2011/0118600 | A1 | 5/2011 | Gertner |
| 2011/0118726 | A1 | 5/2011 | De La Rama et al. |
| 2011/0130708 | A1 | 6/2011 | Perry et al. |
| 2011/0137155 | A1 | 6/2011 | Weber et al. |
| 2011/0144479 | A1 | 6/2011 | Hastings et al. |
| 2011/0146673 | A1 | 6/2011 | Keast et al. |
| 2011/0166499 | A1 | 7/2011 | Demarais et al. |
| 2011/0178570 | A1 | 7/2011 | Demarais |
| 2011/0200171 | A1 | 8/2011 | Beetel et al. |
| 2011/0202098 | A1 | 8/2011 | Demarais et al. |
| 2011/0207758 | A1 | 8/2011 | Sobotka et al. |
| 2011/0208096 | A1 | 8/2011 | Demarais et al. |
| 2011/0257523 | A1 | 10/2011 | Hastings et al. |
| 2011/0257564 | A1 | 10/2011 | Demarais et al. |
| 2011/0257622 | A1 | 10/2011 | Salahieh et al. |
| 2011/0257641 | A1 | 10/2011 | Hastings et al. |
| 2011/0257642 | A1 | 10/2011 | Griggs, III |
| 2011/0263921 | A1 | 10/2011 | Vrba et al. |
| 2011/0264011 | A1 | 10/2011 | Wu et al. |
| 2011/0264075 | A1 | 10/2011 | Leung et al. |
| 2011/0264086 | A1 | 10/2011 | Ingle |
| 2011/0264116 | A1 | 10/2011 | Kocur et al. |
| 2011/0270238 | A1 | 11/2011 | Rizq et al. |
| 2011/0306851 | A1 | 12/2011 | Wang |
| 2011/0319809 | A1 | 12/2011 | Smith |
| 2011/0319968 | A1 | 12/2011 | Hastings et al. |
| 2012/0029496 | A1 | 2/2012 | Smith |
| 2012/0029500 | A1 | 2/2012 | Jenson |
| 2012/0029505 | A1 | 2/2012 | Jenson |
| 2012/0029509 | A1 | 2/2012 | Smith |
| 2012/0029510 | A1 | 2/2012 | Haverkost |
| 2012/0029511 | A1 | 2/2012 | Smith et al. |
| 2012/0029512 | A1 | 2/2012 | Willard et al. |
| 2012/0029513 | A1 | 2/2012 | Smith et al. |
| 2012/0059241 | A1 | 3/2012 | Hastings et al. |
| 2012/0059286 | A1 | 3/2012 | Hastings et al. |
| 2012/0065506 | A1 | 3/2012 | Smith |
| 2012/0065554 | A1 | 3/2012 | Pikus |
| 2012/0095461 | A1 | 4/2012 | Herscher et al. |
| 2012/0101413 | A1 | 4/2012 | Beetel et al. |
| 2012/0101490 | A1 | 4/2012 | Smith |
| 2012/0101538 | A1 | 4/2012 | Ballakur et al. |
| 2012/0109021 | A1 | 5/2012 | Hastings et al. |
| 2012/0116382 | A1 | 5/2012 | Ku et al. |
| 2012/0116383 | A1 | 5/2012 | Mauch et al. |
| 2012/0116392 | A1 | 5/2012 | Willard |
| 2012/0116438 | A1 | 5/2012 | Salahieh et al. |
| 2012/0116486 | A1 | 5/2012 | Naga et al. |
| 2012/0123243 | A1 | 5/2012 | Hastings |
| 2012/0123258 | A1 | 5/2012 | Willard |
| 2012/0123261 | A1 | 5/2012 | Jenson et al. |
| 2012/0123303 | A1 | 5/2012 | Sogard et al. |
| 2012/0123406 | A1 | 5/2012 | Edmunds et al. |
| 2012/0130289 | A1 | 5/2012 | Demarais et al. |
| 2012/0130345 | A1 | 5/2012 | Levin et al. |
| 2012/0130359 | A1 | 5/2012 | Turovskiy |
| 2012/0130360 | A1 | 5/2012 | Buckley et al. |
| 2012/0130362 | A1 | 5/2012 | Hastings et al. |
| 2012/0130368 | A1 | 5/2012 | Jenson |
| 2012/0130458 | A1 | 5/2012 | Ryba et al. |
| 2012/0136344 | A1 | 5/2012 | Buckley et al. |
| 2012/0136349 | A1 | 5/2012 | Hastings |
| 2012/0136350 | A1 | 5/2012 | Goshgarian et al. |
| 2012/0136417 | A1 | 5/2012 | Buckley et al. |
| 2012/0136418 | A1 | 5/2012 | Buckley et al. |
| 2012/0143181 | A1 | 6/2012 | Demarais et al. |
| 2012/0143293 | A1 | 6/2012 | Mauch et al. |
| 2012/0143294 | A1 | 6/2012 | Clark et al. |
| 2012/0150267 | A1 | 6/2012 | Buckley et al. |
| 2012/0157986 | A1 | 6/2012 | Stone et al. |
| 2012/0157987 | A1 | 6/2012 | Steinke et al. |
| 2012/0157988 | A1 | 6/2012 | Stone et al. |
| 2012/0157989 | A1 | 6/2012 | Stone et al. |
| 2012/0157992 | A1 | 6/2012 | Smith et al. |
| 2012/0157993 | A1 | 6/2012 | Jenson et al. |
| 2012/0158101 | A1 | 6/2012 | Stone et al. |
| 2012/0158104 | A1 | 6/2012 | Huynh et al. |
| 2012/0172837 | A1 | 7/2012 | Demarais et al. |
| 2012/0172870 | A1 | 7/2012 | Jenson et al. |
| 2012/0184952 | A1 | 7/2012 | Jenson et al. |
| 2012/0197198 | A1 | 8/2012 | Demarais et al. |
| 2012/0197252 | A1 | 8/2012 | Deem et al. |
| 2012/0232409 | A1 | 9/2012 | Stahmann et al. |
| 2012/0265066 | A1 | 10/2012 | Crow et al. |
| 2012/0265198 | A1 | 10/2012 | Crow et al. |
| 2013/0012844 | A1 | 1/2013 | Demarais et al. |
| 2013/0012866 | A1 | 1/2013 | Deem et al. |
| 2013/0012867 | A1 | 1/2013 | Demarais et al. |
| 2013/0013024 | A1 | 1/2013 | Levin et al. |
| 2013/0023865 | A1 | 1/2013 | Steinke et al. |
| 2013/0035681 | A1 | 2/2013 | Subramanaim et al. |
| 2013/0066316 | A1 | 3/2013 | Steinke et al. |
| 2013/0085489 | A1 | 4/2013 | Fain et al. |
| 2013/0090563 | A1 | 4/2013 | Weber |
| 2013/0090578 | A1 | 4/2013 | Smith et al. |
| 2013/0090647 | A1 | 4/2013 | Smith |
| 2013/0090649 | A1 | 4/2013 | Smith et al. |
| 2013/0090650 | A1 | 4/2013 | Jenson et al. |
| 2013/0090651 | A1 | 4/2013 | Smith |
| 2013/0090652 | A1 | 4/2013 | Jenson |
| 2013/0096550 | A1 | 4/2013 | Hill |
| 2013/0096553 | A1 | 4/2013 | Hill et al. |
| 2013/0096554 | A1 | 4/2013 | Groff et al. |
| 2013/0096604 | A1 | 4/2013 | Hanson et al. |
| 2013/0110106 | A1 | 5/2013 | Richardson |
| 2013/0116687 | A1 | 5/2013 | Willard |
| 2013/0165764 | A1 | 6/2013 | Scheuermann et al. |
| 2013/0165844 | A1 | 6/2013 | Shuros et al. |
| 2013/0165916 | A1 | 6/2013 | Mathur et al. |
| 2013/0165917 | A1 | 6/2013 | Mathur et al. |
| 2013/0165920 | A1 | 6/2013 | Weber et al. |
| 2013/0165923 | A1 | 6/2013 | Mathur et al. |
| 2013/0165924 | A1 | 6/2013 | Mathur et al. |
| 2013/0165925 | A1 | 6/2013 | Mathur et al. |
| 2013/0165926 | A1 | 6/2013 | Mathur et al. |
| 2013/0165990 | A1 | 6/2013 | Mathur et al. |
| 2013/0172815 | A1 | 7/2013 | Perry et al. |
| 2013/0172872 | A1 | 7/2013 | Subramaniam et al. |
| 2013/0172877 | A1 | 7/2013 | Subramaniam et al. |
| 2013/0172878 | A1 | 7/2013 | Smith |
| 2013/0172879 | A1 | 7/2013 | Sutermeister |
| 2013/0172880 | A1 | 7/2013 | Willard |
| 2013/0172881 | A1 | 7/2013 | Hill et al. |
| 2014/0074083 | A1 | 3/2014 | Horn et al. |

FOREIGN PATENT DOCUMENTS

| | | | |
|---|---|---|---|
| EP | 1180004 | A1 | 2/2002 |
| EP | 1335677 | B1 | 8/2003 |
| EP | 1874211 | A2 | 1/2008 |
| EP | 1906853 | A2 | 4/2008 |
| EP | 1961394 | A2 | 8/2008 |
| EP | 1620156 | B1 | 7/2009 |
| EP | 2076193 | A2 | 7/2009 |
| EP | 2091455 | A2 | 8/2009 |
| EP | 2197533 | A1 | 6/2010 |
| EP | 2208506 | A1 | 7/2010 |
| EP | 1579889 | B1 | 8/2010 |
| EP | 2092957 | B1 | 1/2011 |
| EP | 2349044 | A1 | 8/2011 |
| EP | 2027882 | B1 | 10/2011 |
| EP | 2378956 | A2 | 10/2011 |
| EP | 2037840 | B1 | 12/2011 |
| EP | 2204134 | B1 | 4/2012 |
| EP | 2320821 | B1 | 10/2012 |
| GB | 2456301 | A | 7/2009 |
| JP | 2001513338 | A | 12/2005 |
| WO | WO-9842403 | | 10/1998 |
| WO | 9858588 | A1 | 12/1998 |

(56) References Cited

FOREIGN PATENT DOCUMENTS

| | | | |
|---|---|---|---|
| WO | 9900060 | A1 | 1/1999 |
| WO | 9935986 | | 7/1999 |
| WO | 0047118 | A1 | 8/2000 |
| WO | 0066021 | | 11/2000 |
| WO | 0195820 | | 12/2001 |
| WO | 03026525 | A1 | 4/2003 |
| WO | 2004100813 | A2 | 11/2004 |
| WO | 2004110258 | A2 | 12/2004 |
| WO | 2005041810 | | 5/2005 |
| WO | WO-2006041881 | A2 | 4/2006 |
| WO | 2006105121 | A2 | 10/2006 |
| WO | WO-2007131015 | A2 | 11/2007 |
| WO | 2008014465 | A2 | 1/2008 |
| WO | 2009121017 | A1 | 10/2009 |
| WO | 2010067360 | A2 | 6/2010 |
| WO | 2010102310 | A2 | 9/2010 |
| WO | 2010132703 | | 11/2010 |
| WO | 2011005901 | A2 | 1/2011 |
| WO | 2011053757 | A1 | 5/2011 |
| WO | 2011053772 | A1 | 5/2011 |
| WO | 2011091069 | A1 | 7/2011 |
| WO | 2011130534 | A2 | 10/2011 |
| WO | 2012019156 | A1 | 2/2012 |
| WO | 2013049601 | A2 | 4/2013 |

OTHER PUBLICATIONS

"U.S. Appl. No. 11/381,238, Final Office Action dated Feb. 22, 2010", 7 pgs.
"U.S. Appl. No. 11/381,238, Final Office Action dated Oct. 19, 2010", 6 pgs.
"U.S. Appl. No. 11/381,238, Non Final Office Action dated Jan. 19, 2011", 7 pgs.
"U.S. Appl. No. 11/381,238, Non Final Office Action dated Jun. 23, 2010", 8 pgs.
"U.S. Appl. No. 11/381,238, Non Final Office Action dated Sep. 14, 2009", 8 pgs.
"U.S. Appl. No. 11/381,238, Notice of Allowance dated May 10, 2011", 7 pgs.
"U.S. Appl. No. 11/381,238, Response filed Apr. 19, 2011 to Non Final Office Action dated Jan. 19, 2011", 8 pgs.
"U.S. Appl. No. 11/381,238, Response filed Apr. 22, 2010 to Final Office Action dated Feb. 22, 2010", 8 pgs.
"U.S. Appl. No. 11/381,238, Response filed Aug. 13, 2009 to Restriction Requirement dated Jul. 14, 2009", 21 pgs.
"U.S. Appl. No. 11/381,238, Response filed Sep. 23, 2010 to Non Final Office Action dated Jun. 23, 2010", 8 pgs.
"U.S. Appl. No. 11/381,238, Response filed Dec. 14, 2009 to Non Final Office Action dated Sep. 14, 2009", 11 pgs.
"U.S. Appl. No. 11/381,238, Response filed Dec. 20, 2010 to Final Office Action dated Oct. 19, 2010", 6 pgs.
"U.S. Appl. No. 11/381,238, Restriction Requirement dated Jul. 14, 2009", 8 pgs.
"U.S. Appl. No. 13/226,732, Response filed Jul. 17, 2012 to Non Final Office Action dated Apr. 26, 2012", 8 pgs.
"U.S. Appl. No. 13/226,732, Final Office Action dated Aug. 16, 2012", 7 pgs.
"U.S. Appl. No. 13/226,732, Non Final Office Action dated Apr. 26, 2012", 6 pgs.
"U.S. Appl. No. 13/226,732, Notice of Allowance dated Oct. 30, 2012", 5 pgs.
"U.S. Appl. No. 13/226,732, Response filed Oct. 16, 2012 to Final Office action dated Aug. 16, 2012", 7 pgs.
"U.S. Appl. No. 13/226,732, Response to Restriction Requirement dated Mar. 12, 2012", 9 pgs.
"U.S. Appl. No. 13/226,732, Restriction Requirement dated Mar. 12, 2012", 7 pgs.
"European Application Serial No. 7783078.4, Office Action dated May 13, 2009", 3 pgs.
"European Application Serial No. 7783078.4, Office Action dated Aug. 3, 2010", 4 pgs.
"European Application Serial No. 7783078.4, Response filed Sep. 15, 2009 to Office Action dated May 13, 2009", 5 pgs.
"European Application Serial No. 7783078.4, Response filed Dec. 13, 2010 to Office Action dated Aug. 3, 2010", 9 pgs.
"International Application Serial No. PCT/US2007/067989, International Search Report dated Dec. 7, 2007", 4 pgs.
"International Application Serial No. PCT/US2007/067989, Written Opinion dated Dec. 7, 2007", 6 pgs.
"Japanese Application Serial No. 2009-510044, Amendment filed Oct. 15, 2010", (w/ English Translation of Amended Claims), 7 pgs.
"Japanese Application Serial No. 2009-510044, Office Action dated Mar. 21, 2012", 6 pgs.
"Japanese Application Serial No. 2009-510044, Response filed Jul. 20, 2012 to Office Action dated Mar. 21, 2012", With English Claims, 6 pgs.
Dev, N. B, et al., "Intravascular Electroporation Markedly Attenuates Neointima Formation After Balloon Injury of the Carotid Artery in the Rat", Journal of Interventional Cardiology, 13(5), (Oct. 2000), 331-338.
CardioVascular Technologies Inc., "Heated Balloon Device Technology," 11 pages, 2008.
Strategic Business Development, Inc., "Thermal and Disruptive Angioplasty: A Physician's Guide," 8 pages, 1990.
Zhang et al., "Non-contact Radio-Frequency Ablation for Obtaining Deeper Lesions," IEEE Transaction on Biomedical Engineering, vol. 50, No. 2, 6 pages, Feb. 2003.
Lazebnik et al., "Tissue Strain Analytics Virtual Touch Tissue Imaging and Qualification," Siemens Whitepaper, Oct. 2008, 7 pages.
Han et al., "Third-Generation Cryosurgery for Primary and Recurrent Prostate Caner," BJU International, vol. 93, pp. 14-18, 2004.
Zhou et al., "Mechanism Research of Cryoanalgesia," Forefront Publishing Group, 1995.
Florete, "Cryoblative Procedure for Back Pain," Jacksonville Medicine, Oct. 1998, 10 pages.
Stevenson, "Irrigated RF Ablation: Power Titration and Fluid Management for Optimal Safety Efficacy," 2005, 4 pages.
Giliatt et al., "The Cause of Nerve Damage in Acute Compression," Trans Am Neurol Assoc, 1974: 99; 71-4.
Omura et al., "A Mild Acute Compression Induces Neurapraxia in Rat Sciatic Nerve," The International Journal of Neuroscience, vol. 114 (12), pp. 1561-1572, Dec. 2004.
Baun, "Interaction with Soft Tissue," Principles of General & Vascular Sonography, Chapter 2, pp. 23-24, Before Mar. 2012.
Blue Cross Blue Shield Medical Policy, "Surgery Section—MRI-Guided Focused Ultrasound (MRgFUS) for the Treatment of Uterine Fibroids and Other Tumors," 2005, 5 pages.
Gentry et al., "Combines 3D Intracardiac Echo and Ultrasound Ablation," Medical Imaging 2003: Ultrasonic and Signal Processing, vol. 5035, 2003, pp. 166-173.
Lafon et al., "Optmizing the Shape of Ultrasound Transducers for Interstitial Thermal Ablations," MEd Phys. Mar. 2002; 29(3): 290-7 (abstract only).
G. Ter Haar, "Ultrasound Focal Beam Surgery," Ultrasound in Med. & Biol., 1995, vol. 21, No. 9, pp. 1089-1100.
Seip et al., "Transurethral High Intensity Focused Ultrasound: Catheter Based Prototypes and Experimental Results," IEEE Ultrasonics Symposium Proceeding, 2000, 4 pages.
Toytman et al., "Tissue Dissection with Ultrafast Laser Using Extended and Multiple Foci," SPIE Proceeding, Optical Interactions with Tissues and Cells XXI, vol. 7562, 2010, 10 pages.
Zhou et al., "Non-Thermal Ablation of Rabbit Liver VX2 Tumore by Pulsed High Intensity Focused Ultrasound Contrast Agent: Pathological Characteristics," World Journal of Gastroenterology, vol. 14(43), Nov. 21, 2008, pp. 6743-6747.
Van Den Berg, "Light echoes image the human body," OLE, Oct. 2001, p. 35-37.
"IntraLuminal: Products," IntraLuminal Therapeutics, Inc., 2003, p. 1-9.
"Laser Catheter to Aid Coronary Surgery," TechTalk: MIT, Jan. 9, 1991, p. 1-4.

(56) References Cited

OTHER PUBLICATIONS

"Optical Coherence Tomography: LightLab Imaging Starts US Cardiology Clinical Investigations," LightLab Imaging Technology, 2002.
"Optical Coherence Tomography: LightLab Sees Bright Prospects for Cardiac Application of OCT Technology," LightLab Imaging Technology, 2001, vol. 27, No. 35.
"Products—Functional Measurement," VOLCANO Functional Measurement Products US, Mar. 24, 2003, p. 1-2.
Brown et al., "Radiofrequency capacitive heaters: the effect of coupling medium resistivity on power absorption along a mouse leg," Physics in Medicine and Biology, 1993, p. 1-12, vol. 38.
Carrington, "Future of CVI: It's all about plaque: Identification of vulnerable lesions, not 'rusty pipes,' could become cornerstone of preventive cardiology," Diagnostic Imaging, 2001, p. 1-8.
Chen et al., "Percutaneous pulmonary artery denervation completely abolishes experimental pulmonary arterial hypertension in vivo," EuroIntervention, 2013, p. 1-8.
Cimino, "Preventing plaque attack," Mass High Tech, 2001, p. 1-2.
Dahm et al., "Relation of Degree of Laser Debulking of In-Stent Restenosis as a Predictor of Restenosis Rate," The American Journal of Cardiology, 2002, p. 68-70, vol. 90.
De Korte et al., "Characterization of Plaque Components With Intravascular Ultrasound Elastography in Human Femoral and Coronary Arteries In Vitro," Circulation, Aug. 8, 2000, p. 617-623.
Durney et al., "Radiofrequency Radiation Dosimetry Handbook," Oct. 1986, p. 1-2, Fourth Edition.
Durney et al., "Radiofrequency Radiation Dosimetry Handbook: Contents," Oct. 1986, p. 1-5, Fourth Edition.
Fournier-Desseux et al., "Assessment of 1-lead and 2-lead electrode patterns in electrical impedance endotomography," Physiological Measurement, 2005, p. 337-349. Vo. 26, Institute of Physics Publishing.
Fram et al., "Feasibility of Radiofrequency Powered, Thermal Balloon Ablation of Atrioventricular Bypass Tracts Via the Coronary Sinus: In Vivo Canine Studies," PACE, Aug. 1995, p. 1518-1530, vol. 18.
Fram et al., "Low Pressure Radiofrequency Balloon Angioplasty: Evaluation in Porcine Peripheral Arteries," JACC, 1993, p. 1512-1521, vol. 21, No. 6, American College of Cardiology.
Fujimori et al., "Significant Prevention of In-Stent Restenosis by Evans Blue in Patients with Acute Myocardial Infarction," American Heart Association, 2002.
Fujita et al., "Sarpogrelate, An Antagonist of 5-HT(2A) Receptor, Treatment Reduces Restenosis After Coronary Stenting," American Heart Association, 2002.
Gabriel, "Appendix A: Experimental Data," 1999, p. 1-21.
Gabriel, "Appendix C: Modeling the frequency dependence of the dielectric properties to a 4 dispersions spectrum," p. 1-49, Nov. 6, 1997.
Gregory et al., "Liquid Core Light Guide for Laser Angioplasty," The Journal of Quantum Electronics, Dec. 1990, p. 2289-2296, vol. 26, No. 12.
Kaplan et al., "Healing after Arterial Dilatation with Radiofrequency Thermal and Nonthermal Balloon Angioplasty Sytems," Journal of Investigative Surgery, 1993, p. 33-52, vol. 6.
Kolata, "New Studies Question Value of Opening Arteries," The New York Times, Mar. 21, 2004, p. 1-5.
Konings et al., "Development of an Intravascular Impedance Catheter for Detection of Fatty Lesions in Arteries," IEEE Transactions on Medical Imaging, Aug. 1997, p. 439-446, vol. 16, No. 4.
Kurtz et al., "Lamellar Refractive Surgery with Scanned Intrastromal Picosecond and Femtosecond Laser Pulses in Animal Eyes," Journal of Refractive Surgery, Sep./Oct. 1998, p. 541-548.
Lee et al., "Thermal Compression and Molding of Atherosclerotic Vascular Tissue With Use of Radiofrequency Energy: Implications for Radiofrequency Balloon Angioplasty," JACC, 1989, p. 1167-1175, vol. 13, No. 5, American College of Cardiology.
Lima et al., "Efficacy and Safety of Oral Sirolimus to Treat and Prevent In-Stent Restenosis: A Pilot Study Results," American Heart Association, 2002, p. 2929.
Lima et al., "Systemic Immunosuppression Inhibits In-Stent Coronary Intimal Proliferation in Renal Transplant Patients," American Heart Association, 2002, p. 2928.
Morice et al., "A Randomized Comparison of a Sirolimus-Eluting Stent With a Standard Stent for Coronary Revascularization," The New England Journal of Medicine, Jun. 6, 2012, p. 1773-1780, vol. 346, No. 23.
Muller-Leisse et al., "Effectiveness and Safety of Ultrasonic Atherosclerotic Plaque Ablation: In Vitro Investigation," CardioVascular and Interventional Radiology, 1993, p. 303-307, vol. 16.
Nair et al., "Regularized Autoregressive Analysis of Intravascular Ultrasound Backscatter: Improvement in Spatial Accuracy of Tissue Maps," IEEE Transactions on Ultrasonics, Apr. 2004, p. 420-431, vol. 51, No. 4.
Popma et al., "Percutaneous Coronary and Valvular Intervention," Braunwald's Heart Disease: A Textbook of Cardiovascular Medicine, 7th edition, p. 1364-1405, 2005.
Resar et al., "Endoluminal Sealing of Vascular Wall Disruptions With Radiofrequency-Heated Balloon Angioplasty," Catheterization and Cardiovascular Diagnosis, 1993, p. 161-167, vol. 29.
Romer et al., "Histopathology of Human Coronary Atherosclerosis by Quantifying Its Chemical Composition With Raman Spectroscopy," Circulation, 1998, p. 878-885, vol. 97.
Schauerte et al., "Catheter Ablation of Cardiac Autonomic Nerves for Prevention of Vagal Atrial Fibrillation," Circulation, 2000, p. 2774-2780, vol. 102.
Scheller et al., "Intracoronary Paclitaxel Added to Contrast Media Inhibits In-Stent Restenosis of Porcine Coronary Arteries," American Heart Association, 2002, p. 2227.
Scheller et al., "Potential solutions to the current problem: coated balloon," EuroIntervention, 2008, p. C63-C66, vol. 4 (Supplement C).
Shaffer, "Scientific basis of laser energy," Clinics in Sports Medicine, 2002, p. 585-598, vol. 21.
Shmatukha et al., "MRI temperature mapping during thermal balloon angioplasty," Physics in Medicine and Biology, 2006, p. N163-N171, vol. 51.
Slager et al., "Vaporization of Atherosclerotic Plaques by Spark Erosion," J Am Coll Cardiol, 1985, p. 21-25.
Stiles et al., "Simulated Characterization of Atherosclerotic Lesions in the Coronary Arteries by Measurement of Bioimpedance," IEEE Transactions on Biomedical Engineering, Jul. 2003, p. 916-921, vol. 50, No. 7.
Suselbeck et al., "In vivo intravascular electric impedance spectroscopy using a new catheter with integrated microelectrodes," Basic Res Cardiol, 2005, p. 28-34, vol. 100.
Suselbeck et al., "Intravascular electric impedance spectroscopy of atherosclerotic lesions using a new impedance catheter system," Basic Res Cardiol, 2005, p. 446-452, vol. 100.
Tepe et al., "Local Delivery of Paclitaxel to Inhibit Restenosis during Angioplasty of the Leg," The New England Journal of Medicine, 2008, p. 689-699, vol. 358.
"Optical Coherence Tomography: Advantages of OCT," LightLab Imaging Technology, printed Sep. 3, 2003.
"Optical Coherence Tomography: Image Gallery Cardiovascular Procedures," LightLab Imaging Technology, printed Sep. 3, 2003.
"Optical Coherence Tomography: What is OCT?," LightLab Imaging Technology, printed Sep. 3, 2003.
"Optical Coherence Tomography: Why Use OCT?," LightLab Imaging Technology, printed Sep. 3, 2003.
Pieper et al. "Design and implementation of a new computerized system for intraoperative cardiac mapping", J. Appl. Physiol. 71(4): 1529-1539, 1991.

* cited by examiner

CONTROL OF ARTERIAL SMOOTH MUSCLE TONE

CLAIM OF PRIORITY

This application is a continuation of and claims the benefit of priority under 35 U.S.C. §120 to Hastings et al., U.S. patent application Ser. No. 13/226,732, entitled "Control of Arterial Smooth Muscle Tone," filed on Sep. 7, 2011, now issued as U.S. Pat. No. 8,391,971, which is a continuation of and claims the benefit of priority under 35 U.S.C. §120 to Hastings et al., U.S. patent application Ser. No. 11/381,238, entitled "Control of Arterial Smooth Muscle Tone," filed on May 2, 2006, now issued as U.S. Pat. No. 8,019,435, each of which is hereby incorporated by reference herein in its entirety.

FIELD OF DISCLOSURE

This disclosure relates to medical devices, and in particular, to devices for controlling smooth muscle tone.

BACKGROUND

The arteries and arterioles (collectively referred to as "arterial blood vessels") throughout the body are lined with smooth muscle. This smooth muscle regulates the flow of arterial blood. Relaxation of the smooth muscle dilates the arterial blood vessel, permitting free flow of blood. Contraction of the smooth muscle constricts the arterial blood vessel, thereby constricting the flow of blood.

Relaxation and contraction of smooth muscle also have an effect on blood pressure. Relaxation increases the volume of the arterial blood vessel, thereby reducing blood pressure. Such blood vessels are said to be "vasodilated." Contraction reduces the volume of the arterial blood vessel, thereby increasing blood pressure. Such blood vessels are said to be "vasoconstricted."

When a person suffers a heart attack, a tendency exists for blood pressure to fall. In an effort to counteract this tendency, the autonomic nervous system causes smooth muscles throughout much of the vascular system to contract. The resulting system-wide vasoconstriction raises blood pressure.

Among the vasoconstricted arterial blood vessels are the renal artery and its associated renal arterioles. Constriction of these arterial blood vessels hampers the kidneys' ability to remove excess fluid. As a result, blood volume increases beyond normal levels. The heart, which is already in weakened condition, encounters difficulty pumping this quantity of blood. As a result, this excess blood can accumulate in the heart and cause the heart to pump less efficiently. In addition, the excess fluid can be excreted into the lungs, resulting in pulmonary congestion, which in turn may cause difficulty breathing.

It is possible to provide drugs that reduce blood pressure. But these drugs act systemically and therefore counteract what is, for most parts of the arterial system, an effective response to the drop in blood pressure caused by heart failure.

It is also known that smooth muscle tone may be locally controlled by contacting the arterial wall with an electrode and providing a suitable electrical stimulation. However, this requires that the arterial blood vessel be large enough to permit insertion of an electrode. As a result, it is difficult to use this method to control smooth muscle tone in the arterioles. Moreover, there are often a great many arterioles that will need to be vasodilated. A procedure that relies on contacting the wall of each such arteriole would thus be impractical.

SUMMARY OF INVENTION

The invention is based on the recognition that because the blood is electrically conductive, one can effectively broadcast instructions to smooth muscle tissue lining the arterial blood vessels by using the blood vessels themselves as a communication channel. This is achieved by identifying the location of one or more targeted blood vessels and placing a pair of electrodes in such a way that the path of least resistance for current flowing between the two electrodes includes the targeted blood vessel(s).

In one aspect, the invention features an apparatus for locally controlling smooth muscle tone. The apparatus includes a first electrode for insertion into an artery; a barrier for preventing the first electrode from contacting an arterial wall; a second electrode; a power supply; and a controller for coupling the power supply to the electrodes. The controller is configured to cause the electrode to maintain a waveform for controlling polarization of smooth muscle tone.

Embodiments include those in which the first electrode includes a stent, and those in which the first electrode includes a distal tip of a catheter.

Other embodiments include those in which the second electrode includes conducting pads for placement on the skin of a patient, and those in which the second electrode includes a distal tip of a catheter.

Additional embodiments include those in which the barrier includes a stent defining a lumen for receiving the first electrode, those in which the barrier includes a housing surrounding the first electrode, those in which the barrier includes a cage surrounding the first electrode, and those in which the barrier includes a pair of bumpers disposed on either side of the electrode.

Among the various embodiments are those in which the controller is configured to generate a waveform having pulses of alternating polarity, those in which the controller is configured to generate a waveform having pulses of a single polarity, and those in which controller is configured to generate a waveform that is synchronized with the cardiac cycle.

Certain other embodiments include a sensor for providing data indicative of the cardiac cycle to the controller, and/or a local sensor for providing data indicative of blood pressure local to the first electrode.

In another aspect, the invention features a method for regulating smooth muscle tone within an arterial bed of a patient by inserting a first electrode into an artery of the patient; providing a second electrode at a location selected such that current from the first electrode to the second electrode traverses the arterial bed; and generating a voltage waveform between the first and second electrode. The voltage waveform is selected to control polarization of smooth muscle tissue within the arterial bed.

In some practices of the invention, providing a second electrode includes providing a surface electrode for placement on the patient's skin. In other practices, providing a second electrode includes inserting a second electrode into a patient's vein.

Some practices of the invention also include selecting the artery to be a renal artery, and/or selecting the location of the second electrode to be skin adjacent to the kidney.

A variety of waveforms can be generated. In some practices, generating a voltage waveform includes generating a waveform having an excitation cycle and a cleaning cycle. In others, generating a waveform includes generating an excitation cycle that overlaps the diastole portion of the patient's cardiac cycle.

Additional practices of the invention include synchronizing the waveform with the patient's cardiac cycle.

Additional practices include selecting the arterial bed to be an arterial bed that serves a tumor, and/or selecting the arterial bed to include arteries feeding a hemorrhage and/or selecting the arterial bed to include the penile arteries.

Yet other practices of the invention include obtaining a measurement indicative of systemic hypertension, and generating the voltage waveform in response to the measurement.

Other practices of the invention include generating a positive voltage during the excitation cycle, and generating a negative voltage during the excitation cycle.

Other features and advantages of the invention will be apparent from the following detailed description, the claims, and the accompanying figures, in which:

BRIEF DESCRIPTION OF THE DRAWINGS

FIG. 12 shows a stimulation system that uses a stent as a barrier; and

DETAILED DESCRIPTION

Local control of smooth muscle tone in an arterial bed is achieved by causing electric current to flow through the arterial bed. The resulting current is sufficient in amplitude to locally control the polarization of smooth muscles throughout the arterial bed. Depending on the polarity of the current, smooth muscles can be locally depolarized or hyperpolarized.

Figure 1:
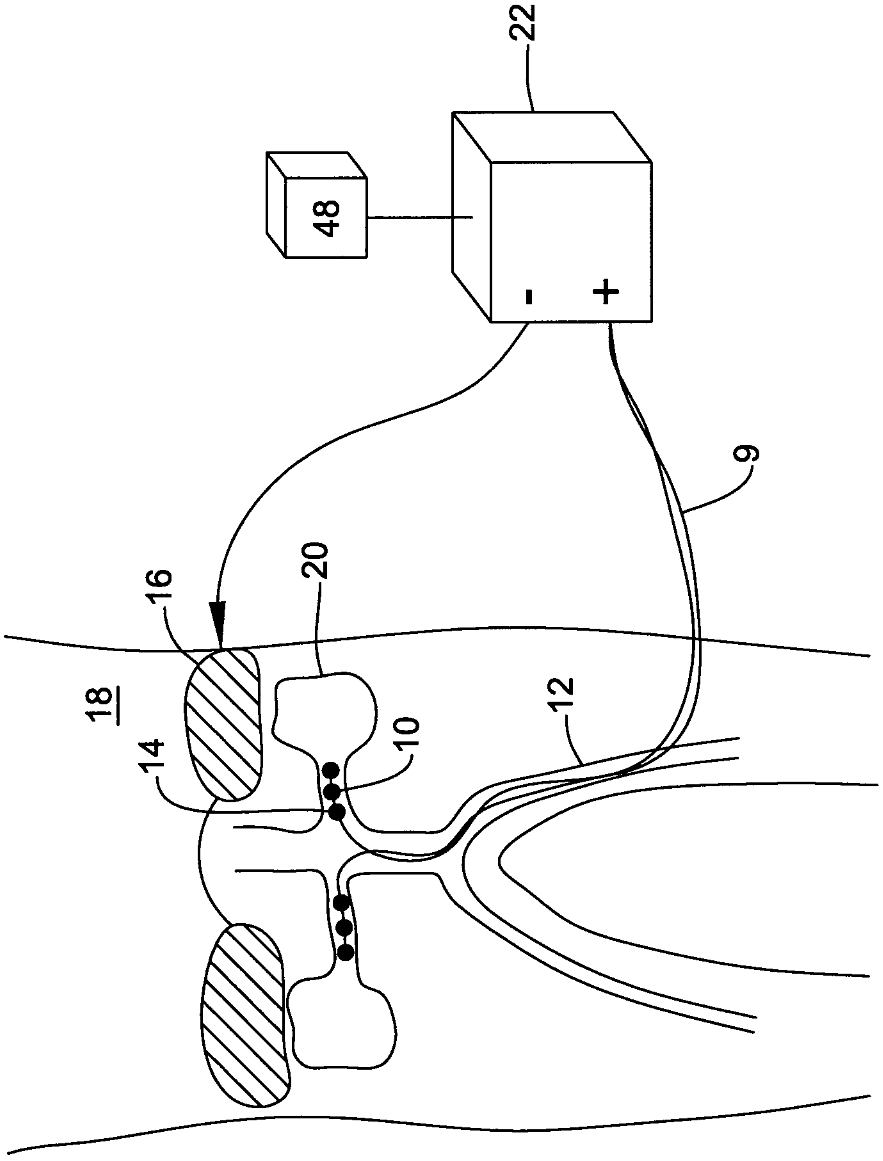
FIGS. 1, 12, and 13 show stimulation systems.

One embodiment, shown in FIG. 1, is intended to locally dilate arterial blood vessels that serve the renal system. This embodiment includes a catheter 9 having a first electrode 10 at its distal tip. The catheter 9 is inserted through a femoral artery 12 and maneuvered until the first electrode 10 reaches a proximal renal artery 14. A second electrode 16 is then placed on the skin 18 adjacent to the kidney 20.

The first and second electrodes 10, 16 are then connected to respective positive and negative terminals of a power supply 22. However, in other applications, in which one seeks to promote vasoconstriction rather than vasodilation, this polarity is reversed. The first and second electrodes 10, 16 are thus monopolar electrodes. However, bipolar or multipolar electrodes can also be used since there is no requirement that all terminals of an electrode be connected to a power supply 22.

In some embodiments, the first electrode 10 is a bare portion of an otherwise electrically insulated guide wire. However, in such cases, there remains a possibility of contact between the first electrode 10 and the arterial wall. Such contact would result in some current flowing into the arterial wall instead of remaining in the bloodstream to reach arterioles downstream from the first electrode 10.

FIG. 1 thus shows one representative embodiment of a catheter 9 having one or more electrodes 10 for placement within a blood vessel that feeds a targeted arterial bed. Current from the catheter-borne electrodes 10 flows through the arterial bed on its way to a return electrode pad placed on the patient's skin over the region supplied by the targeted arterial bed. To achieve vasodilation, the catheter-born electrode 10 is operated as an anode, and the return electrode pad 10 is operated as a cathode. To achieve vasoconstriction, the return electrode pad 10 is operated as an anode, and the catheter-borne electrode 10 is operated as a cathode. The catheter-borne electrode 10 and the return electrode pad 16 are configured so that the electric field lines, and therefore current flow, traverse the target arterial bed.

Figure 2:
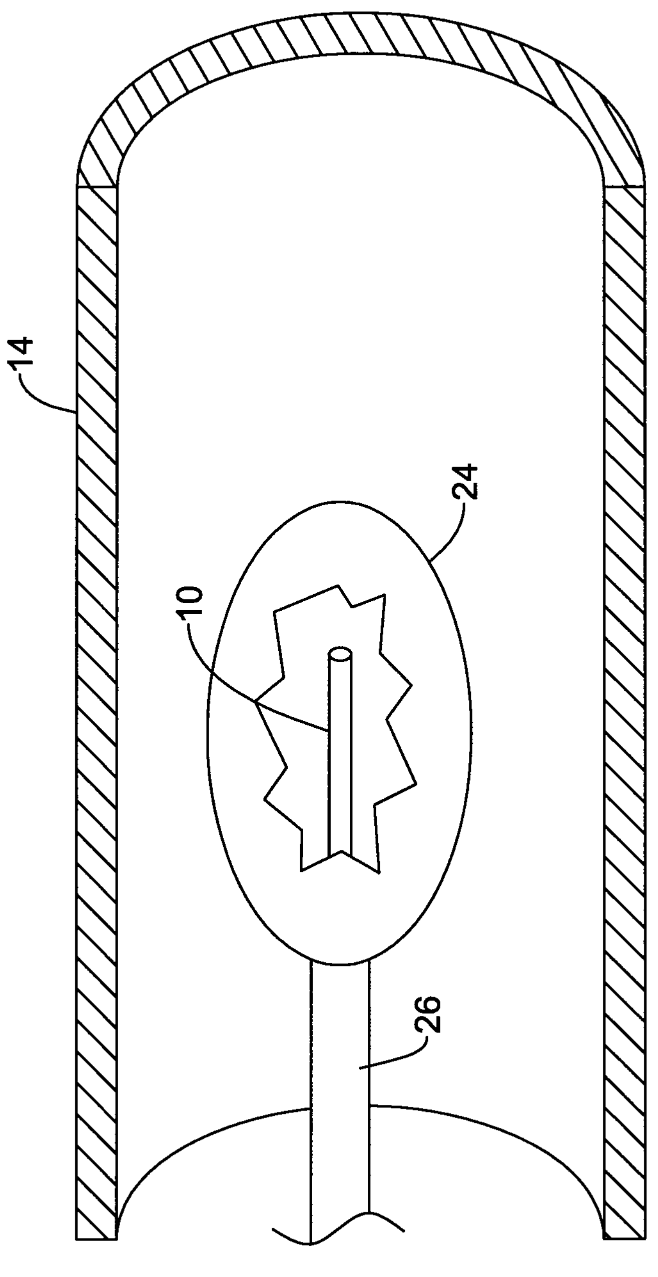
FIG. 2 shows a balloon enclosing the electrode from the stimulation systems of FIG. 1, 12, or 13.

In other embodiments a barrier surrounds the first electrode 10. A suitable barrier, shown in FIG. 2, is a balloon 24 such as those used in a balloon catheter. This balloon 24 prevents the first electrode 10 from actually contacting the arterial wall.

Figure 3:
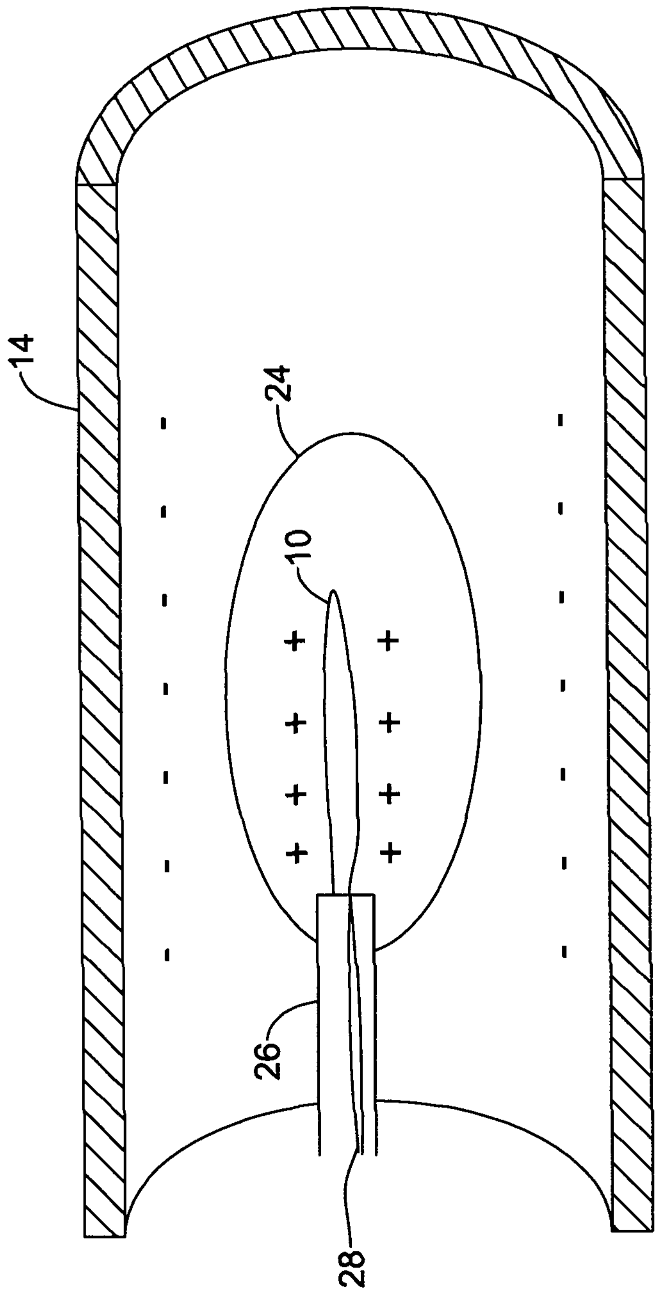
FIGS. 3 and 4 are longitudinal and transverse cross-sections of the balloon of FIG. 2.

FIG. 3 shows a longitudinal cross-section of a balloon catheter 26 with the balloon 24 fully deployed. In the configuration shown, the balloon 24 functions as a barrier to prevent direct contact between the electrode 10 and the wall of the artery 14. The electrode 10 supports an electric field, which in turn provides an electromotive force sufficient to propel current through the bloodstream between the first and second electrodes 10, 16.

Figure 4:
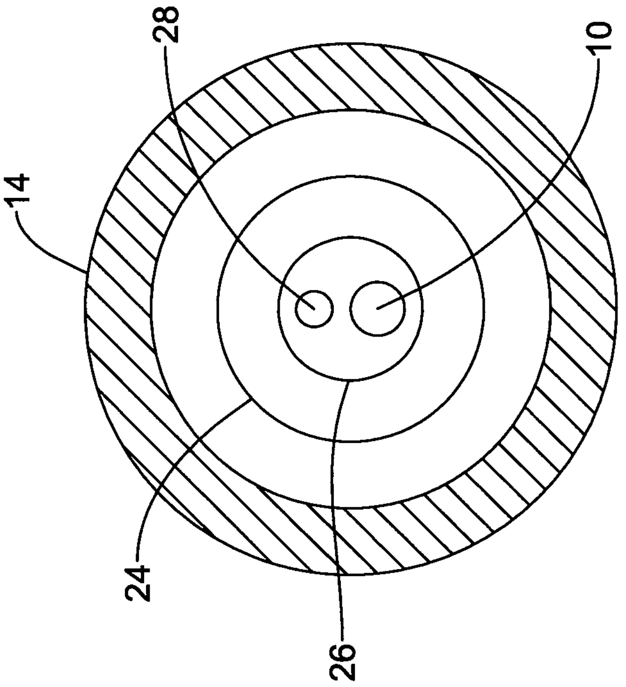

FIG. 4 shows a transverse cross-section of the balloon catheter 26 in FIG. 2. The balloon 24, in its deployed state, has a generally circular cross-section, the radius of which varies along the length thereof, with minima at proximal and distal ends of the balloon 24.

The balloon 24 is inflated with a fluid, which can be gas or liquid, and either electrically insulating or conductive. The pressure of this fluid is selected to provide sufficient turgidity to prevent the electrode 10 from contacting the balloon 24, but enough flexibility to avoid impairing a surgeon's ability to maneuver the catheter 26 through the vascular system.

The balloon 24 is typically made of a biocompatible material, such as latex or silicone. The interior of the balloon 20 is in fluid communication with a pump (not shown) that selectively inflates or deflates the balloon. For this purpose, a flexible tube 28 typically extends along the catheter 26 between the pump and the interior of the balloon 20.

While a balloon 24 as described above will tend to act as a barrier to low-frequency current, at higher frequencies, there may be capacitive coupling between the electrode 10 and the balloon 24. This, in turn, may cause sufficient charge to be on the surface of the balloon 24, in which case contact between the balloon 24 and the arterial wall may result in some current within the wall itself.

Figure 5:
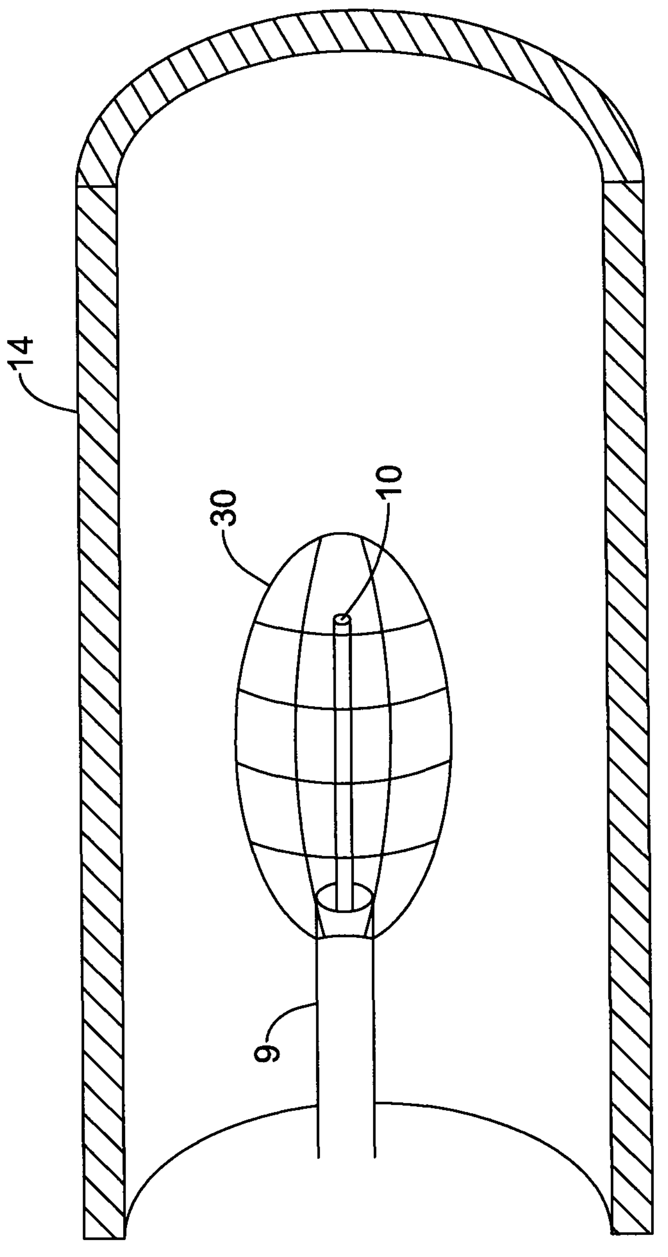
FIG. 5 shows an electrode surrounded by a cage.

Another example of a barrier is a mesh or net cage 30 such as that shown in FIG. 5. The cage 30 can be rigid, or slightly flexible, but with enough resistance to cushion the electrode 10 against accidentally contacting the cage 30. The cage 30 can be made of either an insulating, or a conductive material. However, if the cage 30 is made of a conductive material, it is best electrically isolated from the electrode 10, so that the potential at the electrode 10 need not match the potential of the cage 30.

The overall shape of the cage 30 is similar to that of the balloon 24 shown in FIGS. 2-4. This shape, which is generally ellipsoidal or ovaloid, provides a low profile while reducing the likelihood of trauma should the cage contact the arterial wall.

Figure 6:
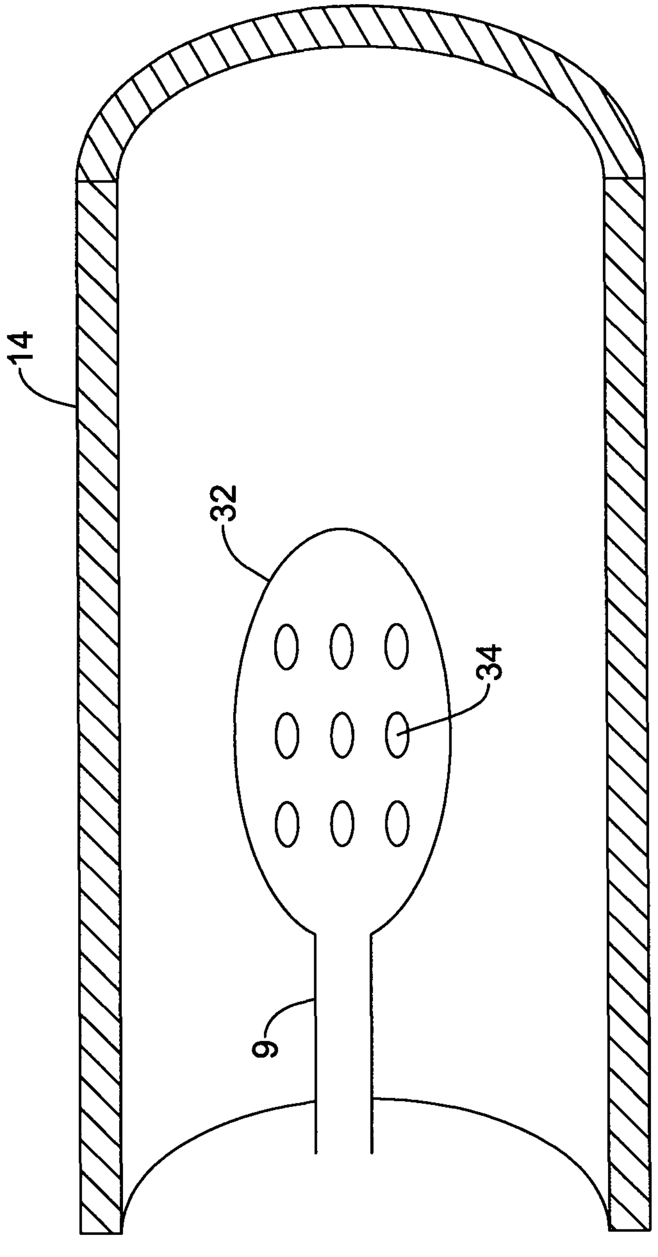
FIG. 6 shows an electrode surrounded by a housing.

Yet another example of a barrier, shown in FIG. 6, is a housing 32 that encloses the electrode 10. The housing can completely enclose the electrode 10, or it can have holes 34, as shown in FIG. 6, through which blood can enter and exit the housing 32, thereby providing direct electrical contact between the electrode and the blood. The housing 32 likewise has an ellipsoidal or ovaloid shape to provide both a low profile and to avoid trauma should the housing inadvertently contact the arterial wall.

Figure 7:
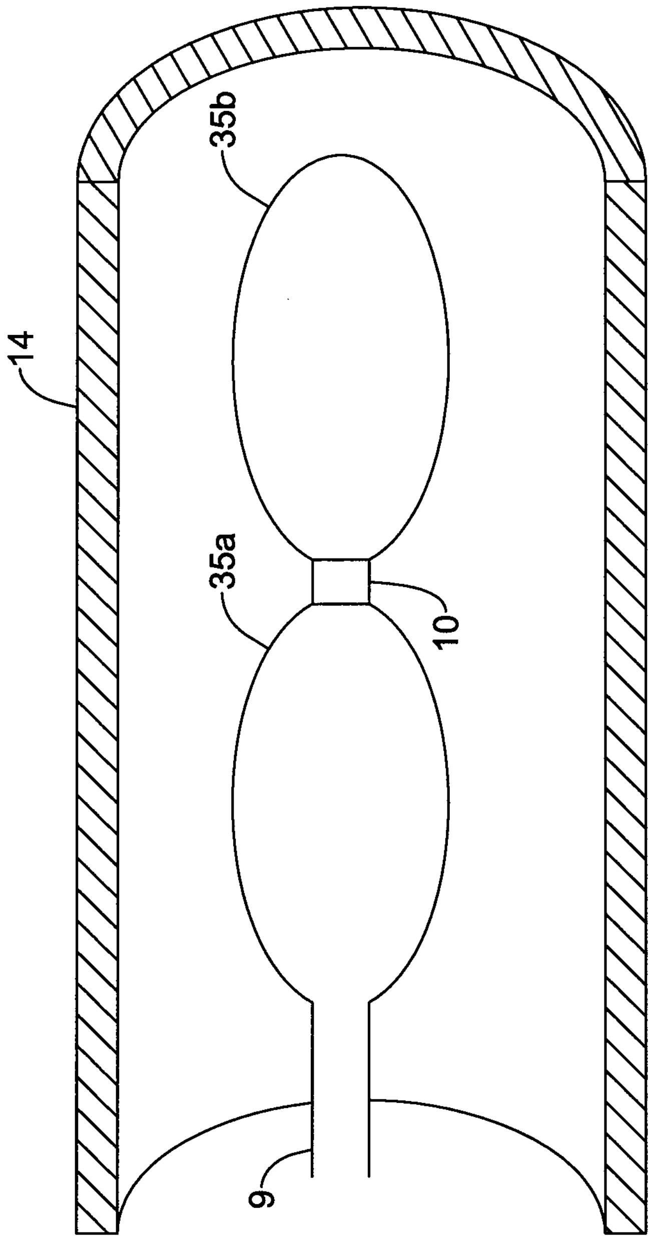
FIG. 7 shows an electrode protected by a pair of bumpers.

Another embodiment, shown in FIG. 7, includes a barrier in the form of a pair of bumpers 35*a*, 35*b* disposed proximal and distal to the first electrode 10. In this embodiment, the electrode 10 contacts the blood directly, while the bumpers 35*a*, 35*b* prevent the electrode 10 from contacting the arterial wall.

Figure 8:
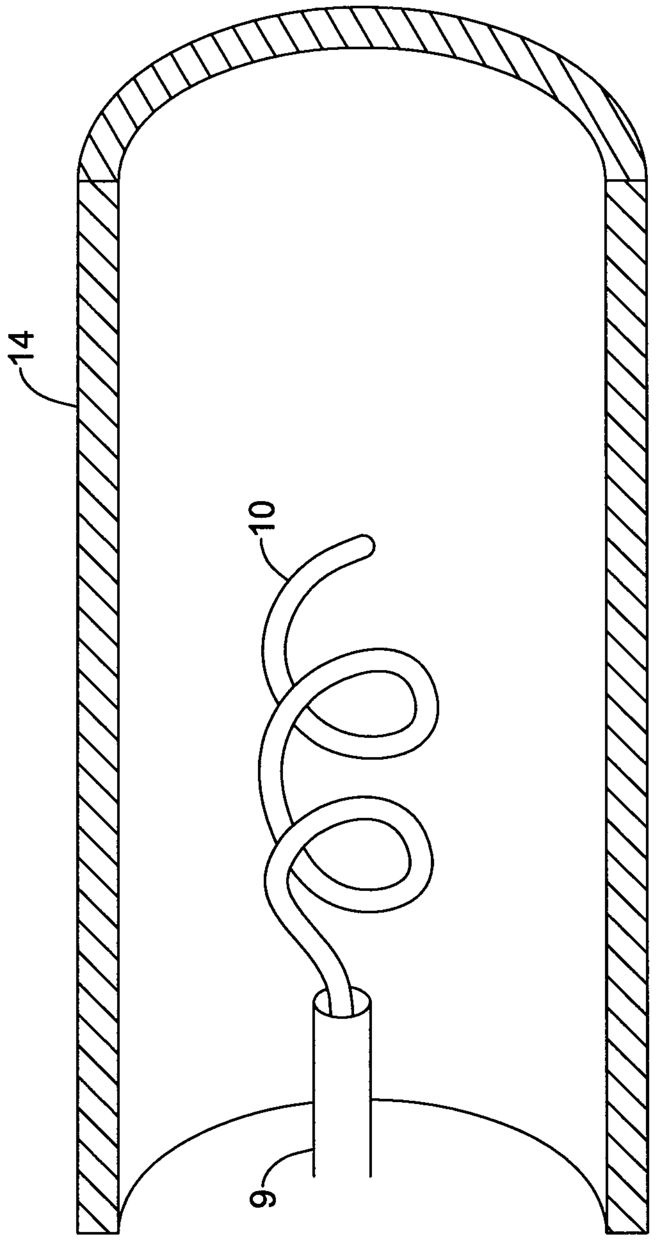
FIG. 8 shows a non-linear electrode.

In the embodiments described thus far, the electrode 10 has been a straight length of wire. However, suitable electrodes can assume any number of shapes. For example an electrode 60 might be helical, as shown in FIG. 8. Such an electrode provides greater surface area for electrical contact, while remaining compact enough to be readily maneuvered.

Electrodes that have a non-linear shape, such as that shown in FIG. 8, can be configured to retract into a sheath. Such retraction enables a surgeon to more easily maneuver the distal tip of the catheter to its destination. In such cases, there exists a mechanism to cause the electrode 10 to assume its desired shape when extended outside of the sheath.

One such mechanism includes an electrode guide-wire made of a shape-memory alloy to which the electrode 10 is mechanically coupled. In such a case, the shape-memory alloy is configured to have, as its remembered shape, the desired shape of the electrode 10. When the electrode guide-wire and the electrode 10 are retracted into the sheath, both are fully extended. When the electrode guide-wire, is extended out of the sheath, it assumes its remembered shape, thereby causing the electrode, to which it is mechanically coupled, to likewise assume that shape. Alternatively, the electrode 10 can itself be made of a shape-memory alloy, in which case no electrode guide-wire is necessary.

Figure 9:
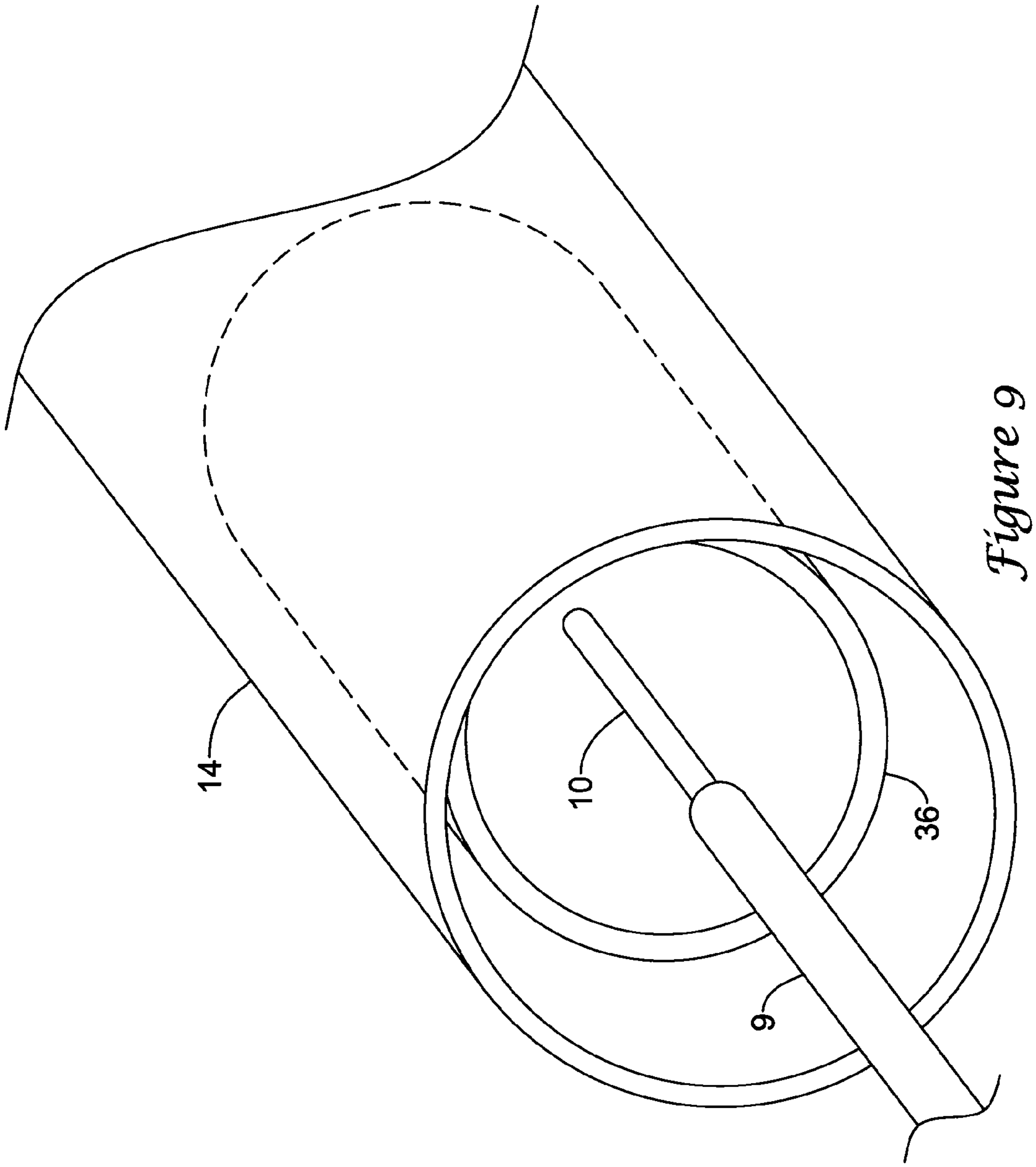
FIG. 9 shows an electrode placed within a lumen defined by a stent.

The first electrode 10 can also be prevented from touching the arterial wall by first implanting an insulated stent 36 in the region in which electrical activation is planned, as shown in FIG. 9. Then, the first electrode 10 is inserted through the artery 14 until it reaches the stent 36. Since the stent 36 is made of an insulating material, it functions as a barrier to current.

Figure 10:
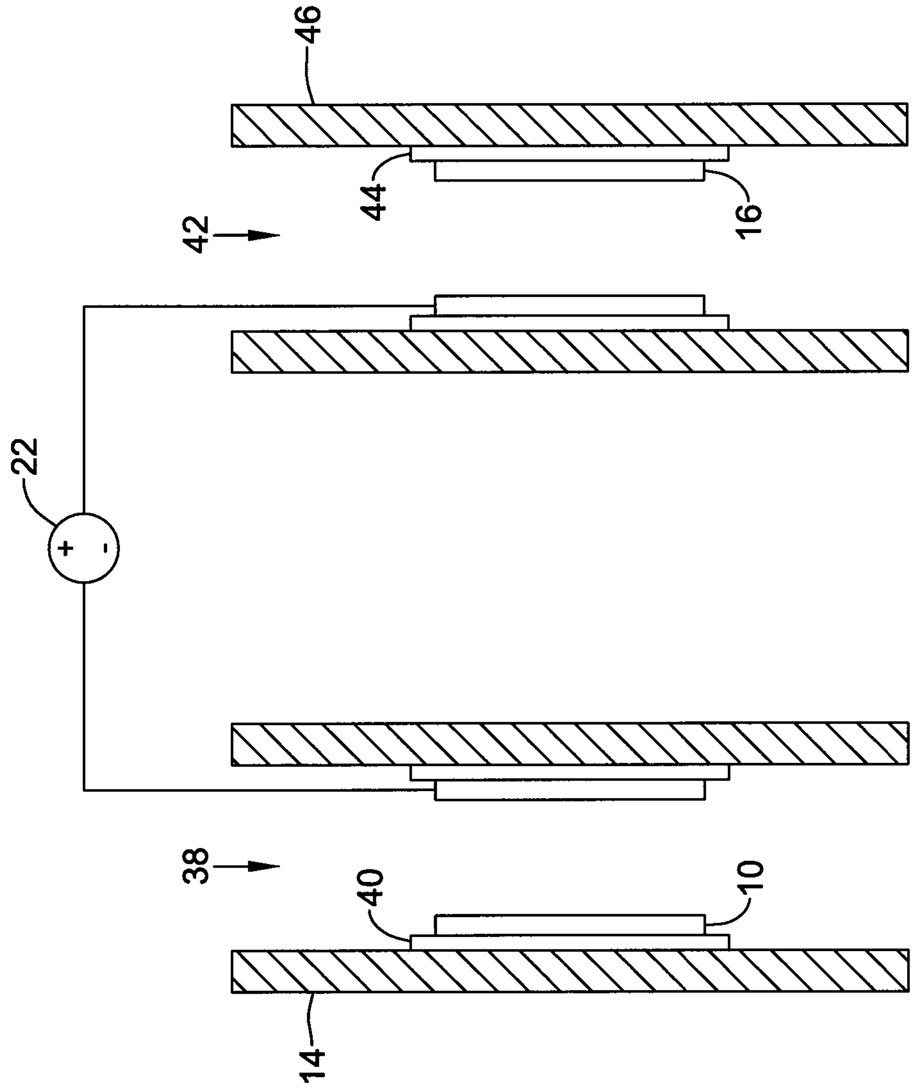
FIG. 10 shows a stimulation system that uses a pair of stents as electrodes.

FIG. 10 shows a longitudinal cross-section of another embodiment in which a stent 38 includes an insulating layer 40 on which is placed a cylindrical first electrode 10. A cylindrical second electrode 16 can be placed on an additional stent 42 having a similar insulation layer and placed in another blood vessel 46 elsewhere in the vascular system. An implanted power supply 22 provides a voltage difference between the two electrodes 10, 16. Stent-mounted electrodes of this type are disclosed in copending U.S. application Ser. No. 10/951,213 filed on Sep. 27, 2004, the contents of which are herein incorporated by reference.

FIG. 9 is representative of a more general configuration in which a first electrode 10 is implanted in an artery feeding a targeted arterial bed, and a second electrode 16 is implanted in a vein draining the targeted arterial bed. The power supply 22, which is typically an energy storage element or battery, together with any control electronics, is mounted near either one of the implanted electrodes 10, 16 and connected to the other implanted electrode 16, 10 with a conductive, insulated wire. Alternatively, the power supply 22 and any control electronics are implanted in a third location and connected to the implanted electrodes 10, 16 by conductive, insulated wires. The power supply 22 can be recharged by an external source of energy, such as an RF transmitter. Alternatively, the power supply 22 can be recharged by an implanted bioelectric generator that transforms body motion or body heat into electrical energy. In some cases, the implanted electrodes 10, 16 are powered entirely from an external power supply 22 such as an RF transmitter. The implanted control electronics may be programmed from outside the body.

As shown in FIG. 1, the second electrode 16 can be a surface electrode, such as a conductive pad placed on the skin. A second electrode 16 placed on the skin is particularly useful for treatment of acute episodes of unwanted vasoconstriction. For treatment of chronic vasoconstriction, the second electrode 16 can be placed in a convenient vein, as suggested by FIG. 10, or in tissue. The relative placement of the first and second electrodes 10, 16 is selected such that the path of least electrical resistance between the two electrodes 10, 16 includes the arterial blood vessels that are to be dilated.

Once the power supply 22 is turned on, a controller 48, shown in FIG. 1, modulates the flow of electric current from the first electrode 10 to the second electrode 16. On its way, the electric current passes through the renal artery 14, and through the remainder of the arterial blood vessels serving the renal system. This electric current flows past smooth muscle cells lining the renal artery 14 and arterioles. The presence of positive charge is believed to hyperpolarize these smooth muscle cells, thereby causing them to relax. This, in turn, would be expected to dilate the arterial blood vessels serving the renal system. As a result, the kidneys 20 would be able to remove excess fluid from the blood even as the remainder of the vascular system remains vasoconstricted.

In the configuration shown in FIG. 1, the polarity of the electric field is such as to hyperpolarize the endothelial cells. Since a change in the membrane potential of the endothelial cells is transmitted across gap junctions to the underlying smooth muscle cells, it is possible to inhibit contraction of the smooth muscle by hyperpolarizing the endothelium alone.

Figure 11:
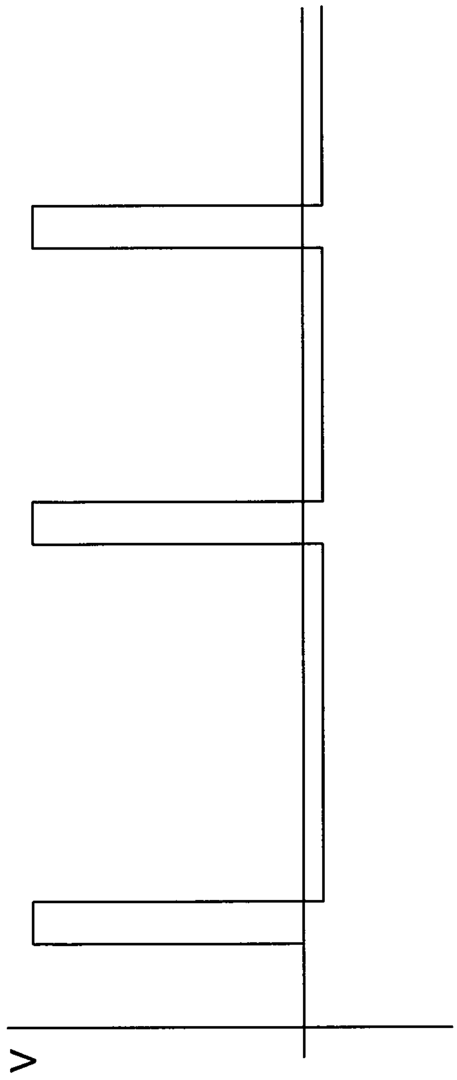
FIG. 11 shows an excitation waveform for use in the stimulation systems of FIGS. 1, 12 and 13.

FIG. 11 shows a typical voltage waveform provided to the first electrode 10. The controller 48 causes the power supply 22 to maintain a large positive voltage during diastole and a small negative voltage at all other times. The optional negative voltage is particularly useful to reduce fouling of the electrode 10. In some practices, the duration of the negative voltage is chosen so that the charge delivered during the negative portion of the waveform balances the charge delivered during the positive portion of the waveform. Suitable voltages are those that cause an electric field of 50 to 2000 volts/meter. Given the conductivity of blood, this translates to current densities of on the order of 25-1000 amperes/meter$^2$. However, some embodiments maintain voltages of 100 to 1000 volts/meter, which translates into current densities of 50-500 amperes/meter$^2$.

In some practices, at least one property of the voltage waveform is synchronized with heart rate. Synchronization can be achieved using locally measured blood flow, blood pressure, or an ECG (electro-cardiogram) signal.

The positive voltage is typically applied during a period of low blood flow, which in peripheral arteries occurs primarily during diastole. The application of a positive voltage during diastole is believed to be helpful because the higher fluid velocity associated with systole tends to sweep the larger particles in the blood into the center of the artery. Since most of these particles are negatively charged, the higher fluid velocity already leaves the arterial wall naturally hyperpolarized during systole. In contrast, during diastole, with its slower fluid flow velocity, the negatively charged particles tend to congregate on the wall, thereby tending to neutralize the positive charge on the wall. Thus, it is during diastole that inducing positive charges is most helpful for maintaining hyperpolarization.

The waveform of FIG. 11 can be varied. For example, in some implementations, there is no negative voltage. Instead, the electrode 10 is made neutral. In other implementations, the positive pulse is reduced in amplitude and/or extended in duration. In other implementations, the pulses and the cardiac cycle are asynchronous.

In some applications, the polarity of the electrodes is reversed. In such cases, the stimulation is like that shown in FIG. 11, but with polarities reversed. When polarity is reversed, stimulation is typically performed during systole instead of diastole.

The electrical stimulation can also be delivered in a waveform that may contain shaped features and/or pulses having both positive and negative polarity components at one or more frequencies. The electrical stimulation need not be constant. There may be time intervals during which the stimulation is turned off.

Figure 12:
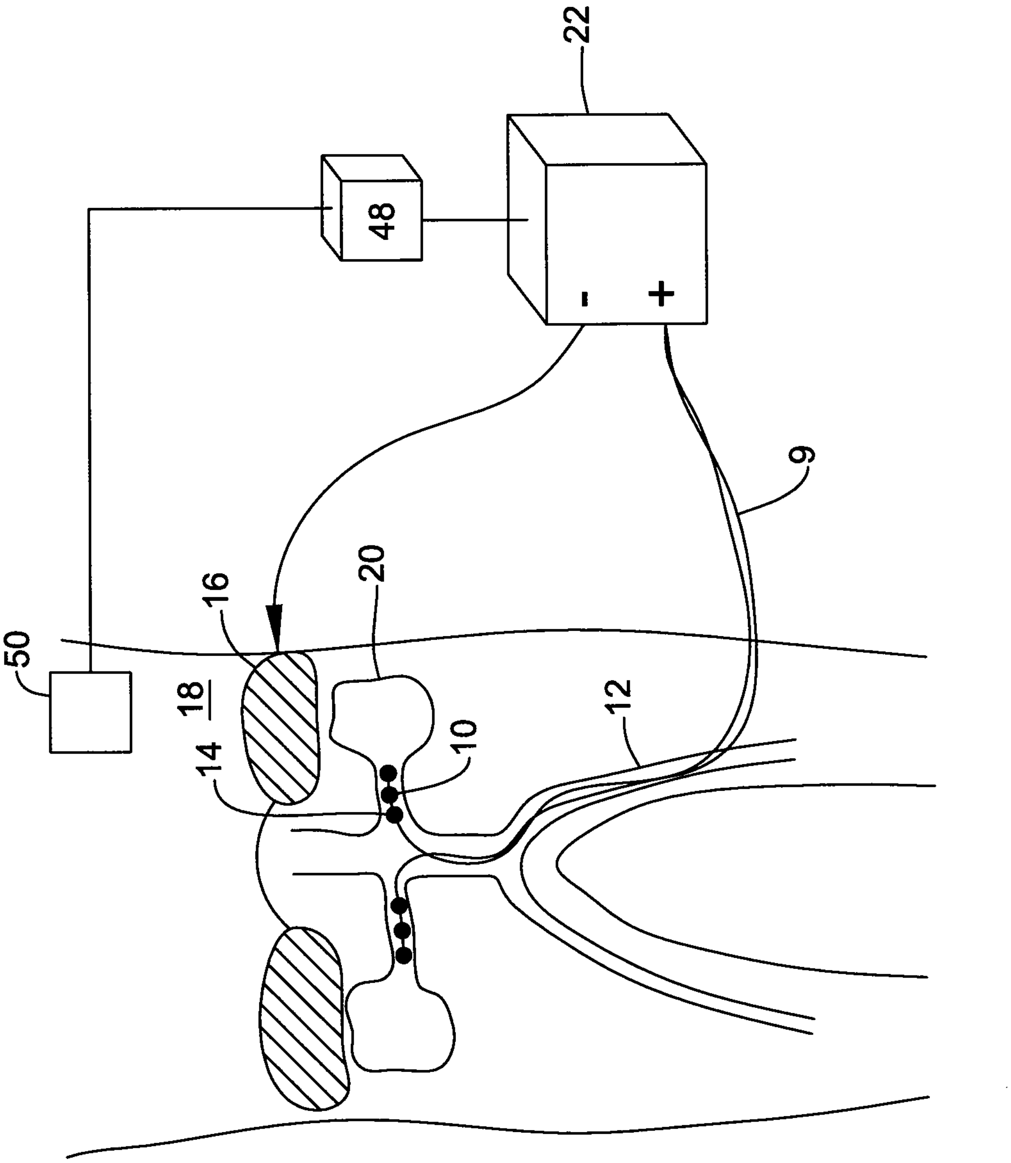

In an alternative embodiment, shown in FIG. 12, the controller 26 is a feedback controller coupled to a sensor 50. The sensor 24 is configured to detect an indicator of the cardiac cycle and to provide cardiac cycle data to the controller 48. Suitable indicators of cardiac cycle include heart beat, blood pressure, flow velocity, or any physical quantity from which the current state of the cardiac cycle can be derived. The controller 48 uses this cardiac cycle data to adaptively vary the interval between the positive pulses shown in FIG. 10. Typical pulse widths range between half the cardiac cycle and 40 milliseconds.

Figure 13:
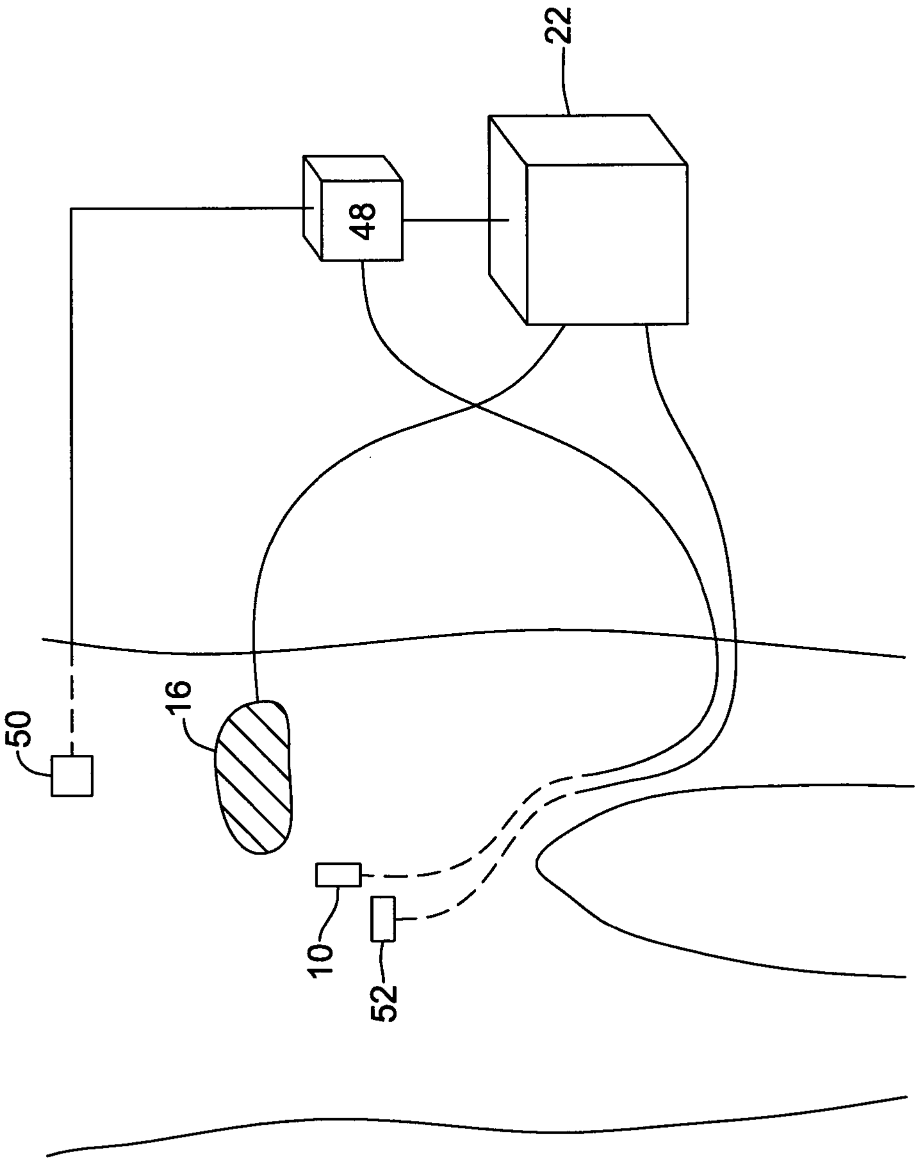

In another embodiment, shown in FIG. 13, the controller 48 receives feedback from a local sensor 52 that measures a property at the target site itself. For example, current flowing in the vicinity of the electrode 10 may have a tendency to heat the surrounding blood. To avoid excessive heating, the local sensor 52 can be a temperature sensor mounted at the distal tip of the catheter. The temperature sensor provides a temperature signal to the controller 48. In response to the temperature signal, the controller 48 regulates the voltage waveform so as to avoid excessive local heating.

Other local characteristics can also be measured by the local sensor 52. For example, the local sensor 52 can be a pressure sensor that provides a pressure signal on the basis of which the controller 48 determines whether a desired local blood pressure has been achieved.

Figure 14:
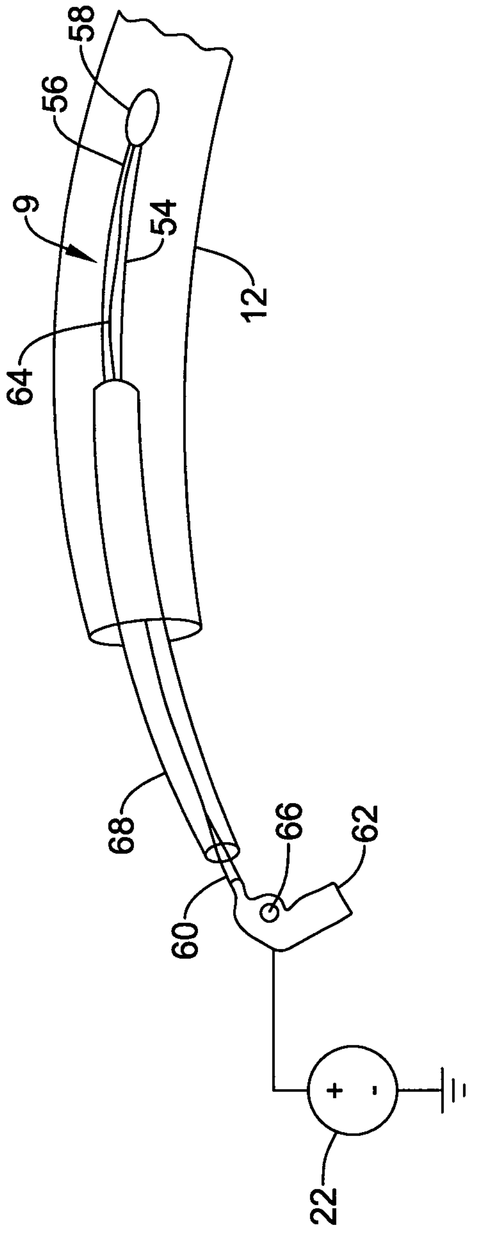
FIG. 14 shows a catheter inserted into a blood vessel.

A typical catheter 9 shown in FIG. 14, features a flexible tube 54 having a distal end 56 connected to a distal tip assembly 58 and a proximal end 60 coupled to a handle 62. Within the distal tip assembly 58 are the first electrode 10 and any of the ancillary structures described above. Extending through the tube 54 is a guide-wire 64, a distal end of which, in some embodiments, also functions as the first electrode 10. A proximal end of the guide-wire 64 is coupled to the handle 62. A trigger 66 mounted on the handle 62 enables a surgeon to selectively connect the power supply 22 to the first and second electrodes 10, 16. Both the catheter 9 and its distal tip assembly 58 are sized and shaped to pass through a cannula 68 inserted into a blood vessel, which in FIG. 14 is the femoral artery 12.

Additional applications of the foregoing configurations include dilating a coronary artery bed distal to an occlusion in patients suffering from acute myocardial infarction. Such dilation may hasten re-perfusion and prevent micro-embolic occlusion of arterioles distal to the occlusion, thereby minimizing loss of myocardium. Dilation of the arterial bed distal to an ischemic stroke may offer the same benefits to affected brain parenchyma. Dilation of vascular beds supplying the lung, for example by an electrode implanted into the pulmonary artery, is useful for treatment of primary pulmonary hypertension. On-demand dilation of penile arteries using a remote-controlled implanted stimulator may help resolve male sexual dysfunction. Systemic hypertension may be controlled by dilation of selected peripheral arterial beds. In this application, implanted electrodes may stimulate dilation in response to an implanted blood pressure sensor, or via remote programming of implanted control circuitry.

In other applications, electrical stimulation can be applied to autonomic nerves to treat a variety of disorders. In such applications, the first and second electrodes 10, 16 are placed near damaged tissue enervated by autonomic nerves. The electrodes 10, 16 are brought near the region either by passing them through a blood vessel that serves that damaged tissue, or by direct insertion into the damaged tissue. Electrical stimulation can be applied to sympathetic or parasympathetic efferent nerves to stimulate or relax tissues respectively, or to afferent nerves to demand attention from the brain or to block signals such as pain from reaching the brain.

For example the apparatus of the present invention can be used to block pain signals originating in nociceptive nerves. When connected to the terminals of the power supply 22, the electrodes 10, 16 cause current to flow into the tissue. This current hyperpolarizes the nociceptive nerves, thereby preventing them from depolarizing. Since the nociceptive nerves provide the sensation of pain to the brain, this hyperpolarization brings about a cessation, or significant diminution, of pain. In addition, current delivered through arterial blood vessels feeding the injured tissue dilates those blood vessels. As a result, more blood is available to nourish the injured tissue, thereby promoting its healing.

The foregoing method of increasing blood supply to nourish selected tissue can be reversed in cases in which one wishes to retard blood flow to, or growth of, selected tissue. Reversal of polarity negatively charges the blood vessel wall, thereby reducing the magnitude of the membrane potential, and potentially causing vasoconstriction. It is additionally possible to induce local constriction at the site of the stimulating electrode by stimulating the sympathetic nerve that constricts the smooth muscle. By selectively constricting arteries, one can reduce flow of arterial blood to selected tissues, thereby inhibiting growth of, and perhaps causing ischemic death of those tissues. This is particularly useful when the selected tissue is, for example, a cancerous tumor, particularly, one that has yet to metastasize. Yet another application of selective vasoconstriction is that of inducing vasoconstriction to reduce blood flow to one or more arteries feeding the site of hemorrhage. This is particularly useful for treating a hemorrhagic stroke.

An apparatus as described herein can be used to deliver a variety of therapies in the acute hospitalization setting. Such therapies include, but are not limited to: selective dilation of one or both renal arterial beds to increase urine output and reduce blood volume; dilation of an arterial bed distal to a blockage in a coronary, cerebral or other artery to provide increased blood flow to ischemic tissue following removal of the offending stenosis, and to allow flushing and passage of micro-emboli through small blood vessels distal to the blockage; and vasoconstriction of arteries feeding the site of a hemorrhagic stroke.

Implanted electrodes as described herein can also be used to deliver therapy chronically or periodically. Such therapies include, but are not limited to: vasodilation of selected peripheral arterial beds to treat systemic hypertension; vasodilation of selected arterial beds to treat local hypertension, for example primary pulmonary hypertension; vasodilation of the penile arteries to treat male sexual dysfunction; and vasoconstriction of an arterial bed feeding a tumor to treat cancer.

Having described the invention, and a preferred embodiment thereof, what we claim as new, and secured by Letters Patent is:

1. An apparatus, comprising:

a catheter comprising a first electrode configured to be fed into a renal artery of a patient;

a temperature sensor disposed adjacent to the first electrode;

a power supply; and an electronic controller configured to couple the power supply to the first electrode;

wherein the controller is configured to deliver a voltage waveform to the first electrode to perform a hypertension treatment;

wherein the controller is configured to synchronize the voltage waveform with the patient's cardiac cycle;

wherein the controller is configured to regulate the voltage waveform based on a temperature signal at a treatment location from the temperature sensor; and wherein the controller is configured to maintain a positive voltage during diastole and a zero or negative voltage at other times.

2. The apparatus of claim 1, wherein the first electrode includes a stent.

3. The apparatus of claim 1, wherein the first electrode includes a distal tip electrode of a catheter.

4. The apparatus of claim 1, further comprising a second electrode configured to be positioned to use blood vessels as communication channels to cause current flowing through conductive blood between the first and second electrodes to traverse a plurality of arterioles in an arterial bed.

5. The apparatus of claim 1, wherein the electronic controller is configured to deliver pulses of alternating polarity through the first electrode.

6. The apparatus of claim 1, wherein the electronic controller is configured to deliver pulses of a single polarity through the first electrode.

7. The apparatus of claim 1 wherein the electrode comprises a helical shape.

8. The apparatus of claim 1, wherein the controller is configured to create an electric field of 50 to 2000 volts/meter.

9. The apparatus of claim 1, wherein the controller is configured to synchronize the voltage waveform with one or more of a blood flow measurement, a blood pressure measurement and an electrocardiogram signal.

10. A method for delivering a hypertension therapy to a patient using a system that comprises a catheter comprising a first electrode and a temperature sensor disposed adjacent to the first electrode, a power supply, and an electronic controller configured to couple the power supply to the first electrode, said method comprising:

inserting the catheter into the patient such that the first electrode is positioned in a renal artery of the patient;

delivering a voltage waveform to the first electrode to perform the hypertension therapy, wherein the voltage waveform is synchronized with the patient's cardiac cycle;

regulating the voltage waveform based on the temperature signal from the temperature sensor; and wherein the voltage waveform comprises a positive voltage during diastole and a zero or negative voltage at other times.

11. The method of claim 10, further comprising inserting the first electrode into a femoral artery to feed the first electrode into the renal artery.

12. The method of claim 10, wherein the first electrode includes a stent.

13. The method of claim 10, wherein the first electrode includes a distal tip electrode of a catheter.

14. The method of claim 10, wherein the voltage waveform comprises pulses of alternating polarity.

15. The method of claim 10, wherein the voltage waveform comprises pulses of a single polarity.

16. The apparatus of claim 10 wherein the electrode comprises a helical shape.

17. The method of claim 10, wherein the voltage waveform creates an electric field of 50 to 2000 volts/meter.

18. The method of claim 10, wherein the voltage waveform is synchronized with one or more of a blood flow measurement, a blood pressure measurement and an electrocardiogram signal.

* * * * *